United States Patent
Schiller et al.

(10) Patent No.: US 8,404,646 B2
(45) Date of Patent: *Mar. 26, 2013

(54) METHODS FOR PREVENTING OR TREATING MITOCHONDRIAL PERMEABILITY TRANSITION

(75) Inventors: Peter W. Schiller, Montreal (CA); Hazel H. Szeto, New York, NY (US); Kesheng Zhao, Jackson Heights, NY (US)

(73) Assignees: Cornell Research Foundation, Inc., New York, NY (US); Institut de Recherches Cliniques de Montreal, Montreal, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/247,648

(22) Filed: Sep. 28, 2011

(65) Prior Publication Data

US 2012/0021970 A1  Jan. 26, 2012

Related U.S. Application Data

(63) Continuation of application No. 12/753,403, filed on Apr. 2, 2010, now abandoned, which is a continuation of application No. 11/427,804, filed on Jun. 30, 2006, now Pat. No. 7,718,620, which is a continuation-in-part of application No. 10/771,232, filed on Feb. 3, 2004, now Pat. No. 7,576,061.

(60) Provisional application No. 60/444,777, filed on Feb. 4, 2003, provisional application No. 60/535,690, filed on Jan. 8, 2004.

(51) Int. Cl.
*A61K 38/07* (2006.01)

(52) U.S. Cl. ............... 514/21.3; 514/21.4; 514/21.5; 514/21.6; 514/21.8; 514/21.9; 530/326; 530/327; 530/328; 530/329; 530/330; 530/331

(58) Field of Classification Search .................. None
See application file for complete search history.

(56) References Cited

U.S. PATENT DOCUMENTS

| | | | |
|---|---|---|---|
| 4,522,811 A | 6/1985 | Eppstein et al. |
| 5,312,899 A | 5/1994 | Schiller |
| 5,602,100 A | 2/1997 | Brown et al. |
| 5,652,122 A | 7/1997 | Frankel et al. |
| 5,674,534 A | 10/1997 | Zale et al. |
| 5,716,644 A | 2/1998 | Zale et al. |
| 5,885,958 A | 3/1999 | Zadina et al. |
| 5,993,848 A | 11/1999 | Suzuki et al. |
| 5,994,372 A | 11/1999 | Yaksh |
| 6,221,355 B1 | 4/2001 | Dowdy |
| 6,268,398 B1 | 7/2001 | Ghosh et al. |
| 6,468,798 B1 | 10/2002 | Debs et al. |
| 6,503,713 B1 | 1/2003 | Rana |
| 6,703,483 B1 | 3/2004 | Schiller |
| 6,759,520 B1 | 7/2004 | Carr et al. |
| 6,900,178 B2 | 5/2005 | Oeltgen et al. |
| 7,498,297 B2 | 3/2009 | Szeto et al. |
| 7,550,439 B2 | 6/2009 | Szeto |
| 7,576,061 B2 | 8/2009 | Szeto et al. |
| 7,718,620 B2 | 5/2010 | Szeto et al. |
| 7,732,398 B2 | 6/2010 | Szeto et al. |
| 7,781,405 B2 | 8/2010 | Szeto |
| 2004/0248808 A1 | 12/2004 | Szeto et al. |
| 2005/0096333 A1 | 5/2005 | Dugar et al. |
| 2005/0158373 A1 | 7/2005 | Szeto et al. |
| 2005/0192215 A1 | 9/2005 | Ghosh et al. |
| 2006/0084606 A1 | 4/2006 | Szeto |
| 2007/0027070 A1 | 2/2007 | Szeto et al. |
| 2007/0027087 A1 | 2/2007 | Szeto et al. |
| 2007/0129306 A1 | 6/2007 | Szeto et al. |

FOREIGN PATENT DOCUMENTS

| | | |
|---|---|---|
| CA | 2361364 | 9/2000 |
| WO | WO-95/22557 | 8/1995 |
| WO | WO-96/40073 | 12/1996 |
| WO | WO-99/15154 | 4/1999 |
| WO | WO-00/38651 | 7/2000 |
| WO | WO-00/55189 | 9/2000 |
| WO | WO-02/05748 | 1/2002 |

OTHER PUBLICATIONS

Lee et al. "The Mechanisms of Neuronal Death Produced by Mitochondrial Toxin 3-Nitropropionic Acid: The Roles of N-Methyl-D-Aspartate Glutamate Receptors and Mitochondrial Calcium Overload." Neuroscience vol. 112, No. 3, pp. 707-716, 2002.*

Crompton, Martin. "The mitochondrial permeability transition pore and its role in cell death." Biochem. J. (1999) 341, 233-249.*

Lemasters et al. "Mitochondrial Dysfunction in the Pathogenesis of Necrotic and Apoptotic Cell Death." Journal of Bioenergetics and Biomembranes, vol. 31, No. 4, pp. 305-319. 1999.*

Friberg et al. "Cyclosporin A, But Not FK 506, Protects Mitochondria and Neurons against Hypoglycemic Damage and Implicates the Mitochondrial Permeability Transition in Cell Death." The Journal of Neuroscience, Jul. 15, 1998, 18(14):5151-5159.*

Notification of Non-Substantial Defects Prior to Notification Prior to Allowance of Israeli Patent Application No. 177030 DTD Dec. 20, 2011.

Azzouz, Mimoun, "Gene Therapy for ALS: Progress and Prospects," Biochemical et Biophysica Acta, 2006, vol. 1762, pp. 112-1127.

(Continued)

*Primary Examiner* — Anish Gupta
(74) *Attorney, Agent, or Firm* — Foley & Lardner LLP

(57) ABSTRACT

The invention provides a method of reducing or preventing mitochondrial permeability transitioning. The method comprises administering an effective amount of an aromatic-cationic peptide having at least one net positive charge; a minimum of four amino acids; a maximum of about twenty amino acids; a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2 a is the largest number that is less than or equal to $p_t+1$, except that when a is 1, $p_t$ may also be 1.

21 Claims, 19 Drawing Sheets

OTHER PUBLICATIONS

Berendsen, Herman, A glimpse of the holy grail?, Science, 282:642-643, Oct. 23, 1998.

Berezowska et al. "Highly potent fluorescent analogoues of the opioid peptide [Dmt1] DALDA." Peptides, Elsevier, Amsterdam 24: 1195-1200 (2003).

Bickel et al., Synthesis and bioactivity of monobiotinylated DALDS: A Mu-specific opioid peptide designed for targeted brain delivery, J Pharmacol and Exp Thereapeutics, 268(2): 791-798 (1994).

Bork, "Powers and Pitfalls in Sequence Analysis: The 70% Hurdle," 2000, Genome Research, vol. 10, pp. 398-400.

Bork, et al., "Go Hunting in Sequence Databases But Watch Out for the Traps," Trends in Genetics, 1996, vol. 12, pp. 425-427.

Bradley, et al., "Limits of Cooperativity in a Structurally Modular Protein: Response of the Notch Ankyrin Domain to Analogous Alanine Substitutions in Each Repeat," J. Mol. Biol., 2002, vol. 324, pp. 373-386.

Brenner, "Errors in Genome Annotation," Trends in Genetics, 1999, vol. 15, pp. 132-133.

Broekemeier, et al., "Inhibition of the Mitochondrial Permeability Transition by Cyclosporin a During Long Time Frame Experiments: Relationship Between Pore Opening and the Activity of mitochondrial Phospholipases," Biochemistry, 1995, vol. 34, pp. 16440-16449.

Censura et al. "The Voltage-dependent Anion Channel is the Target for a New Class of Inhibitors of the Mitochondrial Permeability Transition Pore." J Biol Chem 278(50) 49812-49818 (2003).

Citron, Martin, "Alzheimer's Disease: Treatments in Discovery and Development," Nature Neuroscience Supplement, Nov. 2002, vol. 5, pp. 1055-1057.

Clapp III, et al., "Cardiovascular and Metabolic Responses to Two Receptor-Selective Opioid Agonists in Pregnant Sheep," American Journal of Obstetrics and Gynecology, vol. 178, No. 2, Feb. 1998, pp. 397-401.

Communication from the European Patent Office on EP Application 04707809.2, mailed Jul. 25, 2011.

Corpeleijin et al. Direct association of a promoter polymorphism in the CD36/FAT fatty acid transporter gene with Type 2 diabetes mellitus and insulin resistance, Diabet Med., 23(8):907-911 (2006).

Demas, et al., "Anaesthesia for Heart Transplantation," Br J Anaesth., 1986, vol. 58, pp. 1357-1564.

Dimaio, et al., "Synthesis and Pharmacological Characterization in Vitro of Cyclic Enkephalin Analogues: Effect of Conformational Constraints on Opiate Receptor Selectivity," J. Med. Chem., 1982, vol. 25, pp. 1432-1438.

Doerks, et al., "Protein Annotation: Detective Work for Function Prediction," Trends in Genetics, 1998, vol. 14, pp. 248-250.

Dooley, C T, et al., "Selective Ligands for the Mu, Delta and Kappa Opioid Receptors Identified from a Single Mixture Based Tetrapepide Positional Scanning Combinatinal Library," Journal of Biological Chemistry, American Society of Biochemistry and Molecular Biology, Jul. 24, 1998, Birmingham, US, vol. 273, No. 30, pp. 18848-18856, XP002100725.

Drin, et al., "Studies on the Internalization Mechanism of Cationic Cell-penetrating Peptides," Journal of Biological Chemistry, 2003, vol. 278, No. 33, pp. 31192-31201.

European Office Action in Application No. 04707809.2, dated Dec. 8, 2009.

European Supplemental Search Report for EP 04707809.2, dated Sep. 4, 2009.

File MEDLINE on STN An No: 2005478947. Simmons, Zachary. "Management Strategies for Patients with Amyotrophic Lateral Sclerosis from Diagnosis Through Death." The Neurologist, Sep. 2005, vol. 11, No. 5, pp. 257-270. Abstract only.

Fuhrman, et al., "Oxidative Stress Increases the CD36 Scavenger Receptor and the Cellular Uptake of Oxidized Low-density Lipoprotein in Macrophages from Atherosclerotic Mice: Protective Role of Antioxidants and of Paraoxonase," Atherosclerosis, Mar. 7, 2002, vol. 161, Issue 2, pp. 307-316.

Futaki S et al., "Arginine-Rich Peptides—an Abundant Source of Membrane-Permeable Peptides Having Potential as Carriers for Intracellular Protein Delivery," J. Biol. Chem. 276, 5836-5840 (2001).

Guerrini, et al., "Opioid Receptor Selectivity Alteration by Single Residue Replacement: Synthesis and Activity Profile of [Dmt] Deltorphin B," European Journal of Pharmacology, 1996, vol. 302, pp. 37-42. Abstract only.

Herve, et al., "On the Immunogenic Properties of Retro-Inverso Peptides: Total Retro-Inversion of T-Cell Epitopes Causes a Loss of Binding to MHC II Molecules," Molecular Immunology, 1997, vol. 34, No. 2, pp. 157-163.

Holsey, et al., "Cardiovascular Effects of a μ-Selective Opioid Agonist (Tyrosine-D-Arginine-Phenylalanine-Lysine-NH2) in Fetal Sheep: Sites and Mechanisms of Action," American Journal of Obstetrics and Gynecology, vol. 180, No. 5, May 1999, pp. 1127-1130.

International Search Report and Written Opinion in International Application No. PCT/US2009/33440, dated Apr. 30, 2009.

Kett, et al., "Baroreflex-Mediated Bradycardia But Not Tachycardia is Blunted Peripherally by Intravenous μ-opioid Agonists," American Journal of Obstetrics and Gynecology, vol. 178, No. 5, May 1998, pp. 950-955.

Korczyn, et al., "Emerging Therapies in the Pharmacological Treatment of Parkinson's Disease," Drugs, 2002, vol. 62, No. 5, pp. 775-786.

Lasukova, et al., "Activation of Mu-Opioid Receptors and Cardiomyocyte Resistance to Free Radical Damage," Patol Fiziol Eksp Ter., 2001, vol. 2: Abstract Only; article in Russian.

Lishmanov, et al., "Ligands for Opioid and s-Receptors Improve Cardiac Electrical Stability in Rat Models of Post-Infarction Cardiosclerosis and Stress," Life Sciences, 1999, vol. 65, PL pp. 13-17.

Majer, et al., "Synthesis of Methylated Phenylalanines Via Hydrogenolysis of Corresponding 1, 2, 3, 4 Tetrahydroisoquinoline-3-Caraboxylic Acids," Int. Journal of Peptide & Protein Research, 1994, vol. 43, pp. 62-68.

Margolis, et al., "Diagnosis of Huntington Disease," Clinical Chemistry, 2003, vol. 49, No. 10, pp. 1726-1732.

Moosmann, Bernd and Behl, Christian, Secretory Peptide Hormones are Biochemical Antioxidants: Structure-Activity Relationship, Molecular Pharmacology, vol. 61, No. 2, 2001, pp. 260-268.

Neilan, et al., "Pharmacological Characterization of the Dermorphin Analog [Dmt1]DALDA, a Highly Potent and Selective μ-Opioid Peptide," European Journal of Pharmacology, vol. 419, Issue 1, 2001, pp. 15-23.

Ngo, et al., "Computational Complexity, Protein Structure Prediction, and the Levinthal Paradox," The Protein Folding Problem and Tertiary Structure Prediction, K. Merz, Jr. and S. Le Grand, Editors, Birkhauser Boston, 1994.

Office Action for Canadian Patent Application No. 2,515,080 with Jul. 8, 2010 mail date.

Office Action for Japanese Patent Application No. 2006-503317 with mail date May 24, 2010.

Omoniyi, et al., "A Peripheral Site of Action for the Attenuation of Baroreflex-Mediated Bradycardia by Intravenous μ-Opioid Agonists," Journal of Cardiovascular Pharmacology TM, vol. 35, No. 2, 2000, pp. 269-274.

Pages, et al., "Cystamine and Cysteamine Increase Brain Levels of BDNF in Huntington Disease Via HSJ1b and Transglutaminase," Journal of Clinical Investigation, May 2006, vol. 116, No. 5, pp. 1410-1424.

Patel, et al., "Pharmacotherapy of Cognitive Impairment in Alzheimer's Disease: A Review," J. Geriatr. Psychiatry Neurol., 1995, vol. 8, pp. 81-95.

Richard, et al., "Cell-penetrating Peptides," Journal of Biological Chemistry, 2003, vol. 278, No. 1, pp. 585-590.

Rigobello MP et al. "Effect of polycation ppetides on mitochondrial permeability transition." Biochem Biophys Res Comm. 217(1) 144-149 (1995).

Rudinger, J., "Peptide Hormones," 1976, Ed. J. A. Parson, University Park Press, Baltimore, pp. 1-7.

Schiller, et al., "Dermorphin Analogues Carrying an Increased Positive Net Charge in Their "Message" Domain Display Extremely High µ-Opioid Receptor Selectivity," Journal of Medicinal Chemistry, vol. 32, No. 3, 1989, pp. 698-703.

Schiller, et al., "Opioid Peptide Analogs With Novel Activity Profiles as Potential Therapeutic Agents For Use in Analgesia," First International Peptide Symposium, Program & Abstracts, Nov. 30-Dec. 5, 1997, Kyoto, Japan, 0-36, p. 77.

Schiller, et al., "Opioid peptide analogs with novel activity profiles as potential therapeutic agents for use in analgesia," Peptide Science-Present and Future, Proc. Int. Pept. Symp., 1st, Y. Shimonishi (ed), 1999, pp. 665-669.

Schiller, et al., "Synthesis and in Vitro Opioid Activity Profiles of DALDA Analogues," European Journal of Medicinal Chemistry, vol. 35, Issue 10, Oct. 2000, pp. 895-901.

Schiller, et al., "TIPP: A Highly Potent and Stable Pseudopeptide s Opioid Receptor Antagonist with Extraordinary s Selectivity," J. Med. Chem., 1993, vol. 36, pp. 3182-3187.

Schiller, et al., "Unsulfated C-Terminal 7-Peptide of Cholecystokinin: A New Ligand of the Opiate Receptor," Biochemical and Biophysical Research Communications, 1978, vol. 85, pp. 1332-1338.

Schiller, P.W., et al., "Opioid Peptide Analogs With Novel Activity Profiles as Potential Therapeutic Agents for Use in Analgesia," STN CAPLUS, 1997, No. 132, p. 102403, XP002933635.

Schultz, et al., "Opioids and cardioprotection," Pharmacol Ther., vol. 89, No. 2, pp. 123-137 (2001).

Schwarze, Steven R., et al., "In vivo Protein Transduction: Intracellular Delivery of Biologically Active Proteins, Compounds and DNA," Trends in Pharmacological Sciences, 2001, vol. 21, pp. 45-48.

Second Office Action on Chinese Patent Application 200810177056,9, mailed Nov. 9, 2011.

Shimoyama, et al., "Antinociceptive and Respiratory Effects of Intrathecal H-Tyr-D-Arg-Phe-Lys-NH2 (DALDA) and [Dmt1] DALDA," The Journal of Pharmacology and Experimental Therapeutics, vol. 297, No. 1, Apr. 2001, pp. 364-374.

Shroff, et al., "Effects of Intrathecal Opioid on Extubation Time, Analgesia, and Intensive Care Unit Stay Following Coronary Artery Bypass Grafting," Journal of Clinical Anesthesia, 1997, vol. 9, pp. 415-419.

Skolnick, et al., "From Genes to Protein Structure and Function: Novel Applications of Computational Approaches in the Genomic Era," Trends in Biotech, 2000, vol. 18, No. 1, pp. 34-39.

Smith, et al., "The Challenges of Genome Sequence Annotation or 'The devil is in the details,'" Nature Biotechnology, 1997, vol. 15, pp. 1222-1223.

Song, et al., "A Potent Opiate Agonist Protects Against Myocardial Stunning During Myocardial Ischemia and Reperfusion in Rats," Coronary Artery Disease, 2005, vol. 16, pp. 407-410.

Spetea, Mariana, et al., "Interaction of Agonist Peptide (3H) Tyr-D-Ala-Phe-NH2 With Mu-Opioid Receptor in Rat Brain and CHO-mu/1 Cell Line," Peptides (New York), 1998, vol. 19, No. 6, pp. 1091-1098, XP002410285.

Sriram, et al., "Experimental Allergic Encephalomyelitis: A Misleading Model of Multiple Sclerosis," Ann. Neurol., 2005, vol. 58, pp. 939-945.

Steinman, et al., "How to Successfully Apply Animal Studies in Experimental Allergic Encephalomyelitis to Research on Multiple Sclerosis," Ann Neurol., 2006, vol. 60, pp. 12-21.

Stoessl, Jon A., Potential Therapeutic Targets for Parkinson's Disease., Expert Opin. Ther. Targets, 2008, vol. 12, No. 4, pp. 425-436.

Szeto, et al., "In Vivo Disposition of Dermorphin Analog (DALDA) in Nonpregnant and Pregnant Sheep," The Journal of Pharmacology and Experimental Therapeutics, vol. 284, No. 1, pp. 61-65 (1998).

Szeto, et al., "In Vivo Pharmacokinetics of Selective µ-Opioid Peptide Agonists," The Journal of Pharmacology and Experimental Therapeutics, vol. 298, No. 1, pp. 57-61 (2001).

Szeto, et al., "Mu-Opioid Receptor Densensitization and Resensitization In Vivo," International Narcotics Research Conference, Poster Abstracts, Monday, 1999, Mon19, p. 5.

Szeto, et al., "Respiratory Depression After Intravenous Administration of s-Selective Opioid Peptide Analogs," Peptides, vol. 20, 1999, pp. 101-105.

Tsao L.I. et al.,"Hibernation-induction peptide and cell death: [D-Ala2,D-Leu5]enkephalin blocks Bax-related apoptotic processes," Eur. J. Pharmacol, vol. 428, No. 1, pp. 149-151 (2001).

Vives E et al., "Lipophilic pro-oligonucleotides are rapidly and efficiently internalized in HeLa cells," J. Bio Chem, 272(25): 16010-16017 (1997).

Wells, James A., "Additivity of Mutational Effects in Proteins," Biochemistry, American Chemical Society, Sep. 18, 1990, vol. 29, No. 37.

Wu, et al., "A highly potent peptide analgesic that protects against ischemia-reperfusion-induced myocardial stunning," Am J Physiol Heart Circ Physiol, vol. 283, pp. H783-H791 (2002).

Wu, et al., " Myocardial Protective Effect of Mu Opioid Agonists," International Narcotics Research Conference, Poster Abstracts, Sunday, 1999, Sun59, p. 15.

Zadina J., et al., "A Potent and Selective Endogeneous Agonist for the MU-Opiate Receptor," Nature, Nature Publishing Group, London, GB, Apr. 3, 1997, vol. 386, pp. 499-502, XP002072008.

Zhang, et al., "Oxidative Stress and Genetics in the Pathogenesis of Parkinson's Disease," Neurobiology of Disease, Aug. 2000, vol. 7, Issue 4, pp. 240-250.

Zhao, et al., "Profound Spinal Tolerance After Repeated Exposure to a Highly Selective µ-Opioid Peptide Agonist: Role of s-Opioid Receptors," J. Pharma. Exper. Thera., vol. 302, No. 1, 2002, pp. 188-196.

Zhao, et al.; "Transcellular Transport of a Highly Polar 3+ Net Charge Opioid Tetrapeptide"; Journal of Pharmacology and Experimental Therapeutics (2003); vol. 304(1), pp. 425-432.

Zhao, Kesheng, et al., 1C Transcellular Transport of a Highly Polar 3+ Net Charge Opioid Tetrapepdide, 1D Journal of Pharmacology and Experimental Therapeutics, 1D vol. 304, No. 1, 2003, pp. 425-432.

Zhao, Kesheng, et al., "Translocation of a 3+ Net Charge Tetrapeptide Across Plasma Membrane of Mammalian Cells." Abstract published on-line May 1, 2002 for the World Congress of Pharmacology meeting held Jul. 7, 2002.

Alam, N., et al., "A novel Peptide that Improves Mitochondrial Function Reverses Diabetes-and Age-related Visual Decline," American Aging Association, 2012, Abstract, 1 page.

Alam, N.M., et al., "A Novel Peptide (MTP-131) that Improves Mitochondrial Function Reverses Visual Decline in Mouse Models of Metabolic Dysfunction Leading to Diabetes," American Diabetes Association, 2012, Poster Presentation, 1 page.

Alam, N.M., et al., "Reducing Mitochondrial Oxidative Stress to Treat Diabetes and Age-related Visual Decline," Society of Neuroscience, 2011, Poster Presentation, 1 page.

Anderson, Ethan J. et al., "Mitochondrial H2O2 emission and cellular redox state link excess fat intake to insulin resistance in both rodents and humans," J. Clin. Invest., (Feb. 2009), vol. 119, No. 3, pp. 573-581.

Anderson, Daniel C. et al., "Mitochondrial production of reactive oxygen species contributes to the β adrenergic stimulation of mouse cardiomyocytes," J. Physiol., (2011), 589(7), pp. 1791-1801.

Calkins, Marcus J. et al., "Impaired mitochondrial biogenesis, defective axonal transport of mitochondria, abnormal mitochondrial dynamics and synaptic degeneration in a mouse model of Alzheimer's disease," Hum. Mol. Genet., (2011), vol. 20, No. 23, pp. 4515-4529.

Cao, Mingfeng et al., "Mitochondria-targeted antioxidant attenuates high glucose-induced P38 MAPK pathway activation in human neuroblastoma cells," Mol. Med. Report., (2012), 5(4), pp. 929-934.

Carter, Edward A. et al., "Evaluation of the antioxidant peptide SS31 for treatment of burn-induced insulin resistance," Int. J. Mol. Med., (2011), 28(4), pp. 589-594.

Chen, Min et al., "Mitochondria-targeted peptide MTP-131 alleviates mitochondrial dysfunction and oxidative damage in human trabecular meshwork cells," Invest. Ophthalmol. Vis. Sci., (Sep. 2011), vol. 52, No. 10, pp. 7027-7037.

Cho, Janghyun et al., "Potent mitochondria-targeted peptides reduce myocardial infarction in rats," Coron. Artery Dis., (2007), vol. 18, No. 3, pp. 215-220.

Cho, Sunghee et al., "A novel cell-permeable antioxidant peptide, SS31, attenuates ischemic brain injury by down-regulating CD36," J. Biol. Chem., (Feb. 2007), vol. 282, No. 7, pp. 4634-4642.

Dai, Dao-Fu et al., "Mitochondrial targeted antioxidant peptide ameliorates hypertensive cardiomyopathy," J. Am. Coll. Cardiol., (2011), vol. 58, No. 1, pp. 73-82.

Eirin, A., et. al., "MTP-131 reduces renal injury after percutaneous transluminal renal angioplasty (PTRA) in swine atherosclerotic renal artery stenosis (ARAS)," American Society of Nephrology, 2011, Poster Presentation, 1 page.

Eirin, et al., "A mitochondrial permeability transition pore inhibitor improves renal outcomes after revascularization in experimental atherosclerotic renal artery stenosis," J. Am. Heart Assoc., (2012), vol. 60, pp. 1242-1249; available at http://hyper.ahajournals.org/content/60/5/1242 (8 pages) and supplemental content available at http://hyper.ahajournals.org/content/suppl.2012/10/08/HYPERTENSIONAHA.112.199919DC1.html (18 pages).

Examiner's Report received for Canadian Appln. No. 2,554,166 dated Jul. 9, 2012.

Gilliam, et al., "Doxorubicin acts via mitochondrial ROS to stimulate catabolism in C2C12 Myotubes," Am. J. Physiol. Cell Physiol., (2012), 302(1), pp. C195-C202.

Hale, S.L., et. al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, 2011, Poster Presentation, 1 page.

Han, et al., "Mitochondria-derived reactive oxygen species mediate Heme Oxygenase-1 expression in sheared endothelial cells"; J. Pharmacol. Exp. Ther., (2009), 329(1):94-101.

Kloner, et al., "Reduction of ischemia/reperfusion injury with Bendavia, a mitochondria-targeting cytoprotective peptide," J. Am. Heart Assoc., (2012), vol. 1; available at http://jaha.ahajournals.org/content/1/3/e001644 (14 pages).

Kloner, R.A., et. al., "Bendavia, A Novel Mitochondrial-Targeted Cytoprotective Compound Reduces Ischemia/Reperfusion Injury: Experience in 3 Independent Laboratories," American Heart Association, 2011, 2 pages, Abstract.

Lee, et al., "Novel mitochondria-targeted antioxidant peptide ameliorates burn-induced apoptosis and endoplasmic reticulum stress in the skeletal muscle of mice," Shock, (2011), 36(6), pp. 580-585.

Li, et al., "Mitochondria-targeted antioxidant peptide SS31 attenuates high glucose-induced injury on human retinal endothelial cells," Biochem. Biophys. Res. Commun., (2011), 404(1):349-356.

Liang, X.L., et. al., "SS31 protects human RPE cells from oxidative damage and reduces laser-induced choroidal neovascularization," Association for Research in Vision and Opthamology, 2010, Poster Presentation, 1 page.

Liu, S., et. al., "Boosting mitochondrial function to minimize ischemia-reperfusion injury," Experimental Biology, 2011, Poster Presentation, 1 page.

Ma, et al., "Superoxide flashes: early mitochondrial signals for oxidative stress-induced apoptosis," J. Biol. Chem., (2011), 286(31):27573-27581.

Manczak, et al., "Mitochondria-targeted antioxidants protect against amyloid-β toxicity in Alzheimer's Disease neurons," J. Alzheimer's Dis., (2010), 20(2), pp. S609-S631.

Marcinek, D., et al., "Acute pharmacological intervention reverses mitochondrial deficits and improves function in aged skeletal muscle," American Aging Association, 2012, Abstract, 1 page.

Min, et al., "Mitochondrial-targeted antioxidants protect skeletal muscle against immobilization-induced muscle atrophy," J. Appl. Physiol., (2011), 111(5):1459-1466.

Min, K., et. al., "Mitochondrial-targeted antioxidants attenuate immobilization-induced skeletal muscle atrophy," Experimental Biology, 2011, Abstract, 1 page.

Mizuguchi, et al., "A novel cell-permeable antioxidant peptide decreases renal tubular apoptosis and damage in unilateral ureteral obstruction," Am. J. Physiol. Renal Physiol., 295, (2008), pp. F1545-1553.

Nieborowska-Skorska, et al., "Rac2-MRC-cIII—generated ROS cause genomic instability in chronic myeloid leukemia stem cells and primitive progenitors," Blood, (2012), 119(18), pp. 4253-4263.

Notice of Allowance issued by the Korean Intellectual Property Office in Korean Appln. No. 10-2006-7016975 on Mar. 28, 2012.

Petri, et al., "Cell-permeable peptide antioxidants as a novel therapeutic approach in a mouse model of amyotrophic lateral sclerosis," J. Neurochem., (2006), 98(4), pp. 1141-1148.

Powers, et al., "Mitochondria-targeted antioxidants protect against mechanical-ventilation-induced diaphragm weakness," Crit. Care Med., (2011), 39(7), pp. 1749-1759.

Rabinovitch, P., "Mitochondrial Oxidative Stress and Cardiac Aging," Basic Cardiovascular Sciences, 2011, Presentation, 19 pages.

Reddy, et al., "Toxicity of neurons treated with herbicides and neuroprotection by mitochondria-targeted antioxidant SS31," Int. J. Environ. Res. Public Health, (2011), 8(1), pp. 203-221.

Reddy, P. H., "Amyloid beta Toxicity, Mitochondrial Dysfunction and Synaptic Damage in Alzheimer's Disease: Implications for Mitochondria-Targeted Antioxidant Therapeutics," New York Academy of Sciences, 2010, Abstract, 1 page.

Sharma, et al., "Mitochondrial respiratory complex I dysfunction promotes tumorigenesis through ROS alteration and AKT activation," Hum. Mol. Genet., (2011), 20(23), pp. 4605-4616.

Sloan, et al., "Mitochondrial permeability transition in the diabetic heart: Contributions of thiol redox state and mitochondrial calcium to augmented reperfusion injury," J. Mol. Cell. Cardiol., (2012), 52(5), pp. 1009-1018.

Sullivan et al., "Neurotrophic factors for the treatment of Parkinson's disease," Cytokine & Growth Factor Reviews, vol. 22, issue 3, Jun. 2011, pp. 157-165.

Szeto, "Development of Mitochondria-targeted Aromatic-cationic Peptides for Neurodegenerative Diseases," Ann. N.Y. Acad. Sci., 1147, (2008), pp. 112-121.

Szeto, "Mitochondria-targeted peptide antioxidants: Novel Neuroprotective Agents," The AAPS Journal, 8(3), (2006), pp. E521-E531.

Szeto, et al., "Mitochondria-targeted peptide accelerates ATP recovery and reduces ischemic kidney injury," J. Am. Soc. Nephrol., (2011), 22(6), pp. 1041-1052.

Szeto, et al., "Novel therapies targeting inner mitochondrial membrane—from discovery to clinical development," Pharm. Res., (2011), 28(11), pp. 2669-2679.

Szeto, H., "Cell-permeable, Mitochondrial-targeted, Peptide Antioxidants," The AAPS Journal, (2006), 8(2) Article 32:E277-E283.

Szeto, H., "Mitochondrial Protection as Strategy to treat Ischemia-Reperfusion Injury," American Society of Nephrology, 2010, Presentation, 17 pages.

Szeto, H., "Mitochondria-targeted cytoprotective peptides for ischemia—reperfusion injury," Antioxid Redox Signal, (2008), 10(3):601-619.

Szeto, H.H., "The development of a therapeutic peptide for mitochondrial protection—from bench to bedside," Experimental Biology, 2011, Poster Presentation, 1 page.

Szeto, H.H., et. al., "Rapid Restoration of ATP by SS-31, an Inhibitor of Mitochondrial Permeability Transition, Prevents Tubular Cytoskeletal Rearrangement in Renal Ischemia-Reperfusion Injury," American Siciety of Nephrology, 2010, Poster Presentation, 1 page.

Thomas, et al., "Mitochondrial targeting with antioxidant peptide SS-31 prevents mitochondrial depolarization, reduces islet cell apoptosis, increases islet cell yield, and improves posttransplantation function," J. Am. Soc. Nephroi., (2007), 18(1):213-222.

Tiganis, T., "Reactive Oxygen Species & NAPDH Oxidases in Insulin Signalling," NOX Gordon Research Conference, Jun. 3-8, 2012, Presentation, 44 pages.

US Office Action dated Jun. 19, 2012 in related U.S. Appl. No. 12/843,333.

Wang, et al., "Elevated mitochondrial reactive oxygen species generation affects the immune response via hypoxia-inducible factor-1 α in long-lived Mclk1+/− mouse mutants," J. Immunol., (2010), 184(2), pp. 582-590.

Whiteman, et al., "Do mitochondriotropic antioxidants prevent chlorinative stress-induced mitochondrial and cellular injury?" Antioxid. Redox Signal., (2008), 10(3), pp. 641-650.

Yang, et al., "Mitochondria targeted peptides protect against 1-methyl-4-phenyl-1,2,3,6-tetrahydropyridine neurotoxicity," Antioxid Redox Signal., (2009), 11(9), pp. 2095-2104.

Zhao et al., "Cell-Permeable Peptide Antioxidants Targeted to Inner Mitochondrial Membrane Inhibit Mitochondrial Swelling, Oxidative Cell Death, and Reperfusion Injury", Journal of Biological Chemistry, 279:33, 34682-34690 (Aug. 2004).

Zhao, et al., "Mitochondria-targeted peptide prevents mitochondrial depolarization and apoptosis induced by tert-butyl hydroperoxide in neuronal cell lines," Biochem. Pharmacol., (2005), 70(12), pp. 1796-1806.

* cited by examiner

METHODS FOR PREVENTING OR TREATING MITOCHONDRIAL PERMEABILITY TRANSITION

CROSS-REFERENCE TO RELATED PATENT APPLICATIONS

This application is a continuation of U.S. application Ser. No. 12/753,403, filed Apr. 2, 2010, which is a continuation of U.S. application Ser. No. 11/427,804, filed on Jun. 30, 2006, which is a continuation-in-part of U.S. application Ser. No. 10/771,232, filed on Feb. 3, 2004, which claims priority to U.S. Provisional Application Ser. No. 60/444,777, filed on Feb. 4, 2003, and U.S. Provisional Application No. 60/535,690, filed on Jan. 8, 2004, the contents of which are hereby incorporated by reference in their entirety.

STATEMENT OF GOVERNMENT SUPPORT

This invention was made with government support from the National Institute on Drug Abuse under Grant No. POI DA08924-08. The U.S. Government has certain rights in this invention.

BACKGROUND OF THE INVENTION

Mitochondria exist in virtually all eukaryotic cells, and are essential to cell survival by producing adenosine triphosphate (ATP) via oxidative phosphorylation. Interruption of this vital function can lead to cell death.

Mitochondria also play a major role in intracellular calcium regulation by accumulating calcium ($Ca^{2+}$). Accumulation of calcium occurs in the mitochondria) matrix through a membrane potential-driven uniporter.

The uptake of calcium activates mitochondrial dehydrogenases, and may be important in sustaining energy production and oxidative phosphorylation. In addition, the mitochondria serve as a sink for excessive cytosolic $Ca^{2+}$, thus protecting the cell from $Ca^{2+}$ overload and necrotic death.

Ischemia or hypoglycemia can lead to mitochondrial dysfunction, including ATP hydrolysis and $Ca^{2+}$ overload. The dysfunction causes mitochondrial permeability transition (MPT). MPT is characterized by uncoupling of oxidative phosphorylation, loss of mitochondrial membrane potential, increased permeability of the inner membrane and swelling.

In addition, the mitochondria intermembrane space is a reservoir of apoptogenic proteins. Therefore, the loss of mitochondrial potential and MPT can lead to release of apoptogenic proteins into the cytoplasm. Not surprisingly, there is accumulating evidence that MPT is involved in necrotic and apoptotic cell death (Crompton, *Biochem J.*, 341:233-249 (1999)). Milder forms of cellular insult may lead to apoptosis rather than necrosis.

Cyclosporin can inhibit MPT. Blockade of MPT by cyclosporin A can inhibit apoptosis in several cell types, including cells undergoing ischemia, hypoxia, $Ca^{2+}$ overload and oxidative stress (Kroemer et al., *Annu Rev Physiol.*, 60:619-642 (1998)).

Cyclosporin A, however, is less than optimal as a treatment drug against necrotic and apoptotic cell death. For example, cyclosporin A does not specifically target the mitochondria. In addition, it is poorly delivered to the brain. Furthermore, the utility of cyclosporin A is reduced by its immunosuppressant activity.

The tetrapeptide [Dmt¹]DALDA (2',6'-dimethyltyrosine-D-Arg-Phe-Lys-NH₂, SS-02) has a molecular weight of 640 and carries a net three positive charge at physiological pH. [Dmt¹]DALDA readily penetrates the plasma membrane of several mammalian cell types in an energy-independent manner (Zhao et al., *J Pharmacol Exp Ther.*, 304:425-432, 2003) and penetrates the blood-brain barrier (Zhao et al., *J Pharmacol Exp Ther.*, 302:188-196, 2002). Although [Dmt¹] DALDA has been shown to be a potent mu-opioid receptor agonist, its utility has not been expanded to include the inhibition of MPT.

Thus, there is a need to inhibit MPT in conditions such as ischemia-reperfusion, hypoxia, hypoglycemia, and other diseases and conditions which result in pathological changes as a result of the permeability transitioning of the mitochondrial membranes. Such diseases and conditions include many of the common neurodegenerative diseases.

SUMMARY OF THE INVENTION

These and other objectives have been met by the present invention which provides a method for reducing the number of mitochondria undergoing a mitochondria permeability transition (MPT), or preventing mitochondrial permeability transitioning in any mammal that has need thereof. The method comprises administering to the mammal an effective amount of an aromatic-cationic peptide having:
  a. at least one net positive charge;
  b. a minimum of three amino acids;
  c. a maximum of about twenty amino acids;
  d. a relationship between the minimum number of net positive charges ($p_m$) and the total number of amino acid residues (r) wherein $3p_m$ is the largest number that is less than or equal to r+1; and
  e. a relationship between the minimum number of aromatic groups (a) and the total number of net positive charges ($p_t$) wherein 2a is the largest number that is less than or equal to $p_t$+1, except that when a is 1, $p_t$ may also be 1.

In another embodiment, the invention provides a method for reducing the number of mitochondria undergoing a mitochondrial permeability transition (MPT), or preventing mitochondrial permeability transitioning in a removed organ of a mammal. The method comprises administering to the removed organ an effective amount of an aromatic-cationic peptide having:
  a. at least one net positive charge;
  b. a minimum of three amino acids;
  c. a maximum of about twenty amino acids;
  d. a relationship between the minimum number of net positive charges ($p_m$) and the total number of amino acid residues (r) wherein $3p_m$ is the largest number that is less than or equal to r+1; and
  e. a relationship between the minimum number of aromatic groups (a) and the total number of net positive charges ($p_t$) wherein 2a is the largest number that is less than or equal to $p_t$+1, except that when a is 1, $p_t$ may also be 1.

In yet another embodiment, the invention provides a method of reducing the number of mitochondria undergoing mitochondrial permeability transition (MPT), or preventing mitochondria) permeability transitioning in a mammal in need thereof. The method comprises administering to the mammal an effective amount of an aromatic-cationic peptide having:
  a. at least one net positive charge;
  b. a minimum of three amino acids;
  c. a maximum of about twenty amino acids;
  d. a relationship between the minimum number of net positive charges ($p_m$) and the total number of amino acid residues (r) wherein $3 p_m$ is the largest number that is less than or equal to r+1; and e. a relationship between the minimum number of aromatic groups (a) and the total number of net positive charges ($p_t$) wherein 3a is the largest number that is less than or equal to $p_t+1$, except that when a is 1, $p_t$ may also be 1.

In a further embodiment, the invention provides a method of reducing the number of mitochondria undergoing mitochondrial permeability transition (MPT), or preventing mitochondrial permeability transitioning in a removed organ of a mammal. The method comprises administering to the removed organ an effective amount of an aromatic-cationic peptide having:

a. at least one net positive charge;
b. a minimum of three amino acids;
c. a maximum of about twenty amino acids;
d. a relationship between the minimum number of net positive charges ($p_m$) and the total number of amino acid residues (r) wherein $3p_m$ is the largest number that is less than or equal to r+1; and
e. a relationship between the minimum number of aromatic groups (a) and the total number of net positive charges ($p_t$) wherein 3a is the largest number that is less than or equal to $p_t+1$, except that when a is 1, $p_t$ may also be 1.

BRIEF DESCRIPTION OF THE FIGURES

FIG. 1: Cellular internalization and accumulation of [Dmt$^1$]DALDA (SS-02) in mitochondria.

FIG. 3. [Dmt$^1$]DALDA (SS-02) inhibits mitochondrial swelling and cytochrome c release.

FIG. 4. D-Arg-Dmt-Lys-Phe-NH$_2$ (SS-31) inhibits mitochondrial swelling and cytochrome c release.

DETAILED DESCRIPTION OF THE INVENTION

Figure 1A:
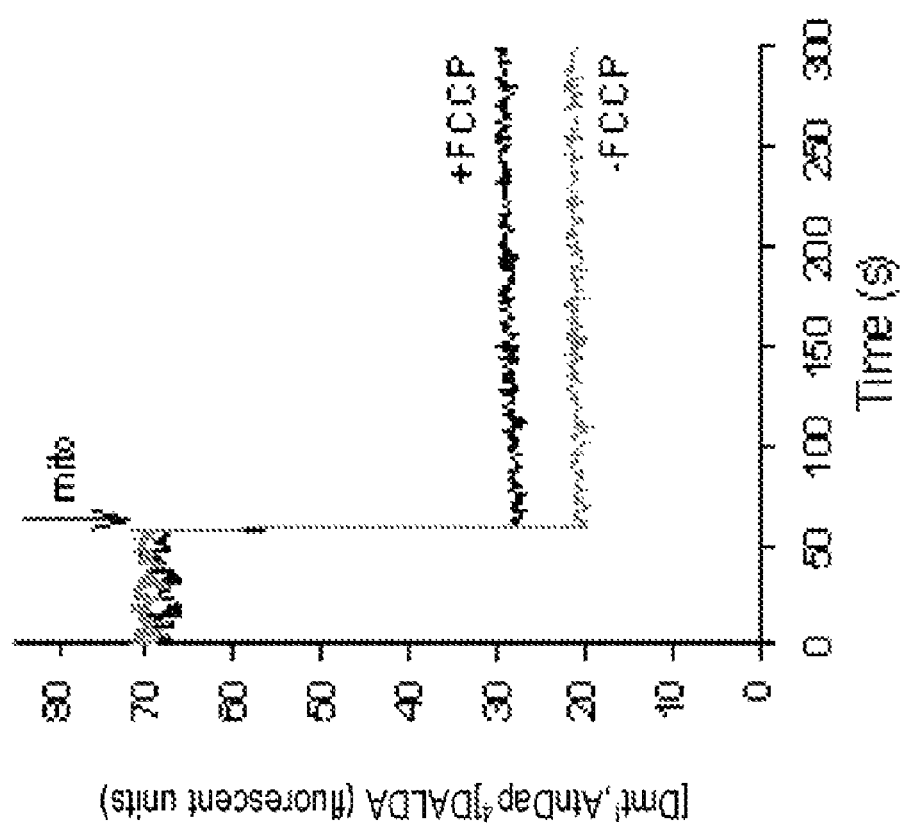
(FIG. 1A) Mitochondrial uptake of SS-19 was determined using fluorescence spectrophotometry (ex/em=320/420 nm). Addition of isolated mouse liver mitochondria (0.35 mg/ml) resulted in immediate quenching of SS-19 fluorescence intensity (gray line). Pretreatment of mitochondria with FCCP (1.5 µM) reduced quenching by <20% (black line).

The invention is based on the surprising discovery by the inventors that certain aromatic-cationic peptides significantly reduce the number of mitochondria undergoing, or even completely preventing, mitochondrial permeability transition (MPT). Reducing the number of mitochondria undergoing, and preventing, MPT is important, since MPT is associated with several common diseases and conditions in mammals. In addition, a removed organ of a mammal is susceptible to MPT. These diseases and conditions are of particular clinical importance as they afflict a large proportion of the human population at some stage during their lifetime.

Peptides

The aromatic-cationic peptides useful in the present invention are water-soluble and highly polar. Despite these properties, the peptides can readily penetrate cell membranes.

The aromatic-cationic peptides useful in the present invention include a minimum of three amino acids, and preferably include a minimum of four amino acids, covalently joined by peptide bonds.

The maximum number of amino acids present in the aromatic-cationic peptides of the present invention is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides useful in the present invention can be any amino acid. As used herein, the term "amino acid" is used to refer to any organic molecule that contains at least one amino group and at least one carboxyl group. Preferably, at least one amino group is at the a position relative to the carboxyl group.

The amino acids may be naturally occurring. Naturally occurring amino acids include, for example, the twenty most common levorotatory (L,) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea.

The peptides useful in the present invention can contain one or more nonnaturally occurring amino acids. The non-naturally occurring amino acids may be L-, dextrorotatory (D), or mixtures thereof. Optimally, the peptide has no amino acids that are naturally occurring.

Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N terminus, the C-terminus, or at any position between the N-terminus and the C-terminus.

The non-natural amino acids may, for example, comprise alkyl, aryl, or alkylaryl groups. Some examples of alkyl amino acids include a-aminobutyric acid, (aminobutyric acid, y-aminobutyric acid, 6-aminovaleric acid, and E-aminocaproic acid. Some examples of aryl amino acids include ortho-, meta, and para-aminobenzoic acid. Some examples of alkylaryl amino acids include ortho-, meta-, and para aminophenyl acetic acid, and y-phenyl-R-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g. methylamine, ethylamine, dimethylamine or dethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D non-naturally occurring amino acids. The D-amino acids do not normally occur in proteins, although they are found in certain peptide antibiotics that are synthesized by means other than the normal ribosomal protein synthetic machinery of the cell, as used herein, the D-amino acids are considered to be non-naturally occurring amino acids.

In order to minimize protease sensitivity, the peptides useful in the methods of the invention should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids.

If the peptide contains protease sensitive sequences of amino acids, at least one of the amino acids is preferably a non-naturally-occurring v-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

It is important that the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r).

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-Arg has one negatively charged amino acid (i.e., Glu) and four positively charged amino acids (i.e., two Arg residues, one Lys, and one His). Therefore, the above peptide has a net positive charge of three.

In one embodiment of the present invention, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

| (r)     | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|----|----|----|----|----|----|----|----|----|----|----|
| ($p_m$) | 1 | 1 | 2 | 2 | 2 | 3 | 3 | 3  | 4  | 4  | 4  | 5  | 5  | 5  | 6  | 6  | 6  | 7  |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

| (r)     | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|----|----|----|----|----|----|----|----|----|----|----|
| ($p_m$) | 2 | 2 | 3 | 3 | 4 | 4 | 5 | 5  | 6  | 6  | 7  | 7  | 8  | 8  | 9  | 9  | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine. For example, the hexapeptide Lys-Gln-Tyr-Arg-Phe-Trp has a net positive charge of two (contributed by the lysine and arginine residues) and three aromatic groups (contributed by tyrosine, phenylalanine and tryptophan residues).

In one embodiment of the present invention, the aromatic-cationic peptides useful in the methods of the present invention have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---------|---|---|---|---|---|---|---|---|---|----|----|----|----|----|----|----|----|----|----|----|
| (a)     | 1 | 1 | 1 | 1 | 2 | 2 | 2 | 3 | 3 | 3  | 4  | 4  | 4  | 5  | 5  | 5  | 6  | 6  | 6  | 7  |

In another embodiment the aromatic-cationic peptides have a relationship between the minimum number of aromatic groups (a) and the total number of net positive charges $(p_t)$ wherein 2a is the largest number that is less than or equal to $p_t+1$. In this embodiment, the relationship between the minimum number of aromatic amino acid residues (a) and the total number of net positive charges $(p_t)$ is as follows:

| $(p_t)$ | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges $(p_t)$ are equal.

Carboxyl groups, especially the terminal carboxyl group of a C-terminal amino acid, are preferably amidated with, for example, ammonia to form the C-terminalamide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-dethyl amido, Nmethyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

Lys-D-Arg-Tyr-$NH_2$,

Phe-D-Arg-His,

D-Tyr-Trp-Lys-$NH_2$,

Trp-D-Lys-Tyr-Arg-$NH_2$,

Tyr-His-D-Gly-Met,

Phe-Arg-D-His-Asp,

Tyr-D-Arg-Phe-Lys-Glu-$NH_2$,

Met-Tyr-D-Lys-Phe-Arg,

D-His-Glu-Lys-Tyr-D-Phe-Arg,

Lys-D-Gln-Tyr-Arg-D-Phe-Trp-$NH_2$,

Phe-D-Arg-I.ys-Trp-Tyr-D-Arg-His,

Gly-D-Phe-Lys-Tyr-His-D-Arg-Tyr-$NH_2$,

Val-D-Lys-His-Tyr-D-Phe-Ser-Tyr-Arg-$NH_2$,

Trp-Lys-Phe-D-Asp-Arg-Tyr-D-His-Lys,

Lys-Trp-D-Tyr-Arg-Asn-Phe-Tyr-D-His-$NH_2$,

Thr-Gly-Tyr-Arg-D-His-Phe-Trp-D-His-Lys,

Asp-D-Trp-Lys-Tyr-D-His-Phe-Arg-D-Gly-Lys-$NH_2$,

D-His-Lys-Tyr-D-Phe-Glu-D-Asp-D-His-D-Lys-Arg-Trp-$NH_2$,

Ala-D-Phe-D-Arg-Tyr-Lys-D-Trp-His-D-Tyr-Gly-Phe,

Tyr-D-His-Phe-D-Arg-Asp-Lys-D-Arg-His-Trp-D-His-Phe,

Phe-Phe-D-Tyr-Arg-Glu-Asp-D-Lys-Arg-D-Arg-His-Phe-$NH_2$,

Phe-Try-Lys-D-Arg-Trp-His-D-Lys-D-Lys-Glu-Arg-D-Tyr-Thr,

Tyr-Asp-D-Lys-Tyr-Phe-D-Lys-D-Arg-Phe-Pro-D-Tyr-His-Lys, Glu-Arg-D-Lys-Tyr-D-Val-Phe-D-His-Trp-Arg-D-Gly-Tyr-Arg-D-Met-$NH_2$,

Arg-D-Leu-D-Tyr-Phe-Lys-Glu-D-Lys-Arg-D-Trp-Lys-D-Phe-Tyr-D-Arg-Gly,

D-Glu-Asp-Lys-D-Arg-D-His-Phe-Phe-D-V al-Tyr-Arg-Tyr-D-Tyr-Arg-His-Phe-$NH_2$,

Asp-Arg-D-Phe-Cys-Phe-D-Arg-D-Lys-Tyr-Arg-D-Tyr-Trp-D-His-Tyr-D-Phe-Lys-Phe,

His-Tyr-D-Arg-Trp-Lys-Phe-D-Asp-Ala-Arg-Cys-D-Tyr-His-Phe-D-Lys-Tyr-His-Ser-$NH_2$,

Gly-Ala-Lys-Phe-D-Lys-Glu-Arg-Tyr-His-D-Arg-D-Arg-Asp-Tyr-Trp-D-His-Trp-His-D-Lys-Asp, and Thr-Tyr-Arg-D-Lys-Trp-Tyr-Glu-Asp-D-Lys-D-Arg-His-Phe-D-Tyr-Gly-Val-Ile-D-His-Arg-Tyr-Lys-$NH_2$.

In one embodiment, the peptides useful in the methods of the present invention have mu-opioid receptor agonist activity (i.e., activate the mu-opioid receptor). Activation of the mu-opioid receptor typically elicits an analgesic effect.

In certain instances, an aromatic-cationic peptide having mu-opioid receptor activity is preferred. For example, during short-term treatment, such as in an acute disease or condition, it may be beneficial to use an aromatic-cationic peptide that activates the mu-opioid receptor. Such acute diseases and conditions are often associated with moderate or severe pain.

In these instances, the analgesic effect of the aromatic cationic peptide may be beneficial in the treatment regimen of the patient or other mammal, although an aromatic-cationic peptide which does not activate the mu-opioid receptor may also be used with or without an analgesic according to clinical requirements.

Alternatively, in other instances, an aromatic-cationic peptide that does not have mu-opioid receptor activity is preferred. For example, during long-term treatment, such as in a chronic disease state or condition, the use of an aromatic-cationic peptide that activates the mu-opioid receptor may be contraindicated. In these instances the potentially adverse or addictive effects of the aromatic-cationic peptide may preclude the use of an aromatic-cationic peptide that activates the mu-opioid receptor in the treatment regimen of a human patient or other mammal.

Potential adverse effects may include sedation, constipation and respiratory depression. In such instances an aromatic-cationic peptide that does not activate the mu-opioid receptor may be an appropriate treatment.

Examples of acute conditions include heart attack, stroke and traumatic injury. Traumatic injury may include traumatic brain and spinal cord injury.

Examples of chronic diseases or conditions include coronary artery disease and any neurodegenerative disorders, such as those described below.

Peptides useful in the methods of the present invention which have mu opioid receptor activity are typically those peptides which have a tyrosine residue or a tyrosine derivative at the N-terminus (i.e., the first amino acid position). Preferred derivatives of tyrosine include 2'-methyltyrosine (Mmt); 2',6'-dimethyltyrosine (2'6'Dmt); 3',5'-dimethyltyrosine (3'5'Dmt); N,2',6'-trimethyl tyrosine (Tmt); and 2'hydroxy-6'-methyltryosine (Hmt).

In a particular preferred embodiment, a peptide that has mu-opioid receptor activity has the formula Tyr-D-Arg-Phe-Lys-NH$_2$ (for convenience represented by the acronym: DALDA, which is referred to herein as SS-01). DALDA has a net positive charge of three, contributed by the amino acids tyrosine, arginine, and lysine and has two aromatic groups contributed by the amino acids phenylalanine and tyrosine. The tyrosine of DALDA can be a modified derivative of tyrosine such as in 2',6'dimethyltyrosine to produce the compound having the formula 2',6'-Dmt-D-Arg-PheLys-NH$_2$ (i.e., Dmt$^1$-DALDA, which is referred to herein as SS-02).

Peptides that do not have mu-opioid receptor activity generally do not have a tyrosine residue or a derivative of tyrosine at the N-terminus (i.e., amino acid position one). The amino acid at the N-terminus can be any naturally occurring or nonnaturally occurring amino acids other than tyrosine.

In one embodiment, the amino acid at the N-terminus is phenylalanine or its derivative. Preferred derivatives of phenylalanine include 2'-methyl phenylalanine (Mmp), 2',6'-dimethylphenylalanine (Dmp), N,2',6'-trimethylphenylalanine (Tmp), and 2'-hydroxy-6'-methylphenylalanine (Hmp).

Other aromatic-cationic peptide that does not have mu-opioid receptor activity has the formula Phe-D-Arg-Phe-Lys-NH$_2$ (i.e., Phe$^1$-DALDA, which is referred to herein as SS-20). Alternatively, the N-terminal phenylalanine can be a derivative of phenylalanine such as 2',6'-dimethylphenylalanine (2'6'Dmp). DALDA containing 2',6'-dimethylphenylalanine at amino acid position one has the formula 2',6'-Dmp-D-Arg-Phe-Lys-NH$_2$ (i.e., 2'6'Dmp$^1$-DALDA).

In a preferred embodiment, the amino acid sequence of Dmt$^1$-DALDA (SS-02) is rearranged such that Dint is not at the N-terminus. An example of such an aromatic-cationic peptide that does not have mu-opioid receptor activity has the formula D-Arg-2'6'Dmt-Lys-Phe-NH$_2$ (referred to in this specification as SS-31).

DALDA, Phe$^1$-DALDA, SS-31, and their derivatives can further include functional analogs. A peptide is considered a functional analog of DALDA, Phe$^1$-DALDA, or SS-31 if the analog has the same function as DALDA, Phe$^1$-DALDA, or SS-31. The analog may, for example, be a substitution variant of DALDA, Phe$^1$-DALDA, or SS-31, wherein one or more amino acid is substituted by another amino acid.

Suitable substitution variants of DALDA, Phe$^1$-DALDA, or SS-31 include conservative amino acid substitutions. Amino acids may be grouped according to their physicochemical characteristics as follows:

a. Non-polar amino acids: Ala(A) Ser(S) Thr(T) Pro(P) Gly(G);

b. Acidic amino acids: Asn(N) Asp(D) Glu(E) Gln(Q);

c. Basic amino acids: His(H) Arg(R) Lys(K);

d. Hydrophobic amino acids: Met(M) Leu(L) Ile(I) Val(V); and e. Aromatic amino acids: Phe(F) Tyr(Y) Trp(W) His(H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of analogs useful in the practice of the present invention that activate mu-opioid receptors include, but are not limited, to the aromatic-cationic peptides shown in Table 1.

TABLE 1

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | NH$_2$ |
| Tyr | D-Arg | Phe | Orn | | NH$_2$ |
| Tyr | D-Arg | Phe | Dab | | NH$_2$ |
| Tyr | D-Arg | Phe | Dap | | NH$_2$ |
| 2'6'Dmt | D-Arg | Phe | Lys | | NH$_2$ |
| 2'6'Dmt | D-Arg | Phe | Lys | Cys | NH$_2$ |
| 2'6'Dmt | D-Arg | Phe | Lys-NH(CH$_2$)$_2$-NH-dns | | NH$_2$ |
| 2'6'Dmt | D-Arg | Phe | Lys-NH(CH$_2$)$_2$-NH-atn | | NH$_2$ |
| 2'6'Dmt | D-Arg | Phe | dnsLys | | NH$_2$ |
| 2'6'Dmt | D-Cit | Phe | Lys | | NH$_2$ |
| 2'6'Dmt | D-Cit | Phe | Ahp | | NH$_2$ |
| 2'6'Dmt | D-Arg | Phe | Orn | | NH$_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 2'6'Dmt | D-Arg | Phe | Dab | | NH₂ |
| 2'6'Dmt | D-Arg | Phe | Dap | | NH₂ |
| 2'6'Dmt | D-Arg | Phe | Ahp (2-aminoheptanoic acid) | | NH₂ |
| Bio-2'6'Dmt | D-Arg | Phe | Lys | | NH₂ |
| 3'5'Dmt | D-Arg | Phe | Lys | | NH₂ |
| 3'5'Dmt | D-Arg | Phe | Orn | | NH₂ |
| 3'5'Dmt | D-Arg | Phe | Dab | | NH₂ |
| 3'5'Dmt | D-Arg | Phe | Dap | | NH₂ |
| Tyr | D-Arg | Tyr | Lys | | NH₂ |
| Tyr | D-Arg | Tyr | Orn | | NH₂ |
| Tyr | D-Arg | Tyr | Dab | | NH₂ |
| Tyr | D-Arg | Tyr | Dap | | NH₂ |
| 2'6'Dmt | D-Arg | Tyr | Lys | | NH₂ |
| 2'6'Dmt | D-Arg | Tyr | Orn | | NH₂ |
| 2'6'Dmt | D-Arg | Tyr | Dab | | NH₂ |
| 2'6'Dmt | D-Arg | Tyr | Dap | | NH₂ |
| 2'6'Dmt | D-Arg | 2'6'Dmt | Lys | | NH₂ |
| 2'6'Dmt | D-Arg | 2'6'Dmt | Orn | | NH₂ |
| 2'6'Dmt | D-Arg | 2'6'Dmt | Dab | | NH₂ |
| 2'6'Dmt | D-Arg | 2'6'Dmt | Dap | | NH₂ |
| 3'5'Dmt | D-Arg | 3'5'Dmt | Arg | | NH₂ |
| 3'5'Dmt | D-Arg | 3'5'Dmt | Lys | | NH₂ |
| 3'5'Dmt | D-Arg | 3'5'Dmt | Orn | | NH₂ |
| 3'5'Dmt | D-Arg | 3'5'Dmt | Dab | | NH₂ |
| Tyr | D-Lys | Phe | Dap | | NH₂ |
| Tyr | D-Lys | Phe | Arg | | NH₂ |
| Tyr | D-Lys | Phe | Lys | | NH₂ |
| Tyr | D-Lys | Phe | Orn | | NH₂ |
| 2'6'Dmt | D-Lys | Phe | Dab | | NH₂ |
| 2'6'Dmt | D-Lys | Phe | Dap | | NH₂ |
| 2'6'Dmt | D-Lys | Phe | Arg | | NH₂ |
| 2'6'Dmt | D-Lys | Phe | Lys | | NH₂ |
| 3'5'Dmt | D-Lys | Phe | Orn | | NH₂ |
| 3'5'Dmt | D-Lys | Phe | Dab | | NH₂ |
| 3'5'Dmt | D-Lys | Phe | Dap | | NH₂ |
| 3'5'Dmt | D-Lys | Phe | Arg | | NH₂ |
| Tyr | D-Lys | Tyr | Lys | | NH₂ |
| Tyr | D-Lys | Tyr | Orn | | NH₂ |
| Tyr | D-Lys | Tyr | Dab | | NH₂ |
| Tyr | D-Lys | Tyr | Dap | | NH₂ |
| 2'6'Dmt | D-Lys | Tyr | Lys | | NH₂ |
| 2'6'Dmt | D-Lys | Tyr | Orn | | NH₂ |
| 2'6'Dmt | D-Lys | Tyr | Dab | | NH₂ |
| 2'6'Dmt | D-Lys | Tyr | Dap | | NH₂ |
| 2'6'Dmt | D-Lys | 2'6'Dmt | Lys | | NH₂ |
| 2'6'Dmt | D-Lys | 2'6'Dmt | Orn | | NH₂ |
| 2'6'Dmt | D-Lys | 2'6'Dmt | Dab | | NH₂ |
| 2'6'Dmt | D-Lys | 2'6'Dmt | Dap | | NH₂ |
| 2'6'Dmt | D-Arg | Phe | dnsDap | | NH₂ |
| 2'6'Dmt | D-Arg | Phe | atnDap | | NH₂ |
| 3'5'Dmt | D-Lys | 3'5'Dmt | Lys | | NH₂ |
| 3'5'Dmt | D-Lys | 3'5'Dmt | Orn | | NH₂ |
| 3'5'Dmt | D-Lys | 3'5'Dmt | Dab | | NH₂ |
| 3'5'Dmt | D-Lys | 3'5'Dmt | Dap | | NH₂ |
| Tyr | D-Lys | Phe | Arg | | NH₂ |
| Tyr | D-Orn | Phe | Arg | | NH₂ |
| Tyr | D-Dab | Phe | Arg | | NH₂ |
| Tyr | D-Dap | Phe | Arg | | NH₂ |
| 2'6'Dmt | D-Arg | Phe | Arg | | NH₂ |
| 2'6'Dmt | D-Lys | Phe | Arg | | NH₂ |
| 2'6'Dmt | D-Orn | Phe | Arg | | NH₂ |
| 2'6'Dmt | D-Dab | Phe | Arg | | NH₂ |
| 3'5'Dmt | D-Dap | Phe | Arg | | NH₂ |
| 3'5'Dmt | D-Arg | Phe | Arg | | NH₂ |
| 3'5'Dmt | D-Lys | Phe | Arg | | NH₂ |
| 3'5'Dmt | D-Orn | Phe | Arg | | NH₂ |
| Tyr | D-Lys | Tyr | Arg | | NH₂ |
| Tyr | D-Orn | Tyr | Arg | | NH₂ |
| Tyr | D-Dab | Tyr | Arg | | NH₂ |
| Tyr | D-Dap | Tyr | Arg | | NH₂ |
| 2'6'Dmt | D-Arg | 2'6'Dmt | Arg | | NH₂ |
| 2'6'Dmt | D-Lys | 2'6'Dmt | Arg | | NH₂ |
| 2'6'Dmt | D-Orn | 2'6'Dmt | Arg | | NH₂ |
| 2'6'Dmt | D-Dab | 2'6'Dmt | Arg | | NH₂ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 3'5'Dmt | D-Dap | 3'5'Dmt | Arg | | $NH_2$ |
| 3'5'Dmt | D-Arg | 3'5'Dmt | Arg | | $NH_2$ |
| 3'5'Dmt | D-Lys | 3'5'Dmt | Arg | | $NH_2$ |
| 3'5'Dmt | D-Orn | 3'5'Dmt | Arg | | $NH_2$ |
| Mmt | D-Arg | Phe | Lys | | $NH_2$ |
| Mmt | D-Arg | Phe | Orn | | $NH_2$ |
| Mmt | D-Arg | Phe | Dab | | $NH_2$ |
| Mmt | D-Arg | Phe | Dap | | $NH_2$ |
| Tmt | D-Arg | Phe | Lys | | $NH_2$ |
| Tmt | D-Arg | Phe | Orn | | $NH_2$ |
| Tmt | D-Arg | Phe | Dab | | $NH_2$ |
| Tmt | D-Arg | Phe | Dap | | $NH_2$ |
| Hmt | D-Arg | Phe | Lys | | $NH_2$ |
| Hmt | D-Arg | Phe | Orn | | $NH_2$ |
| Hmt | D-Arg | Phe | Dab | | $NH_2$ |
| Hmt | D-Arg | Phe | Dap | | $NH_2$ |
| Mmt | D-Lys | Phe | Lys | | $NH_2$ |
| Mmt | D-Lys | Phe | Orn | | $NH_2$ |
| Mmt | D-Lys | Phe | Dab | | $NH_2$ |
| Mmt | D-Lys | Phe | Dap | | $NH_2$ |
| Mmt | D-Lys | Phe | Arg | | $NH_2$ |
| Tmt | D-Lys | Phe | Lys | | $NH_2$ |
| Tmt | D-Lys | Phe | Orn | | $NH_2$ |
| Tmt | D-Lys | Phe | Dab | | $NH_2$ |
| Tmt | D-Lys | Phe | Dap | | $NH_2$ |
| Tmt | D-Lys | Phe | Arg | | $NH_2$ |
| Hmt | D-Lys | Phe | Lys | | $NH_2$ |
| Hmt | D-Lys | Phe | Orn | | $NH_2$ |
| Hmt | D-Lys | Phe | Dab | | $NH_2$ |
| Hmt | D-Lys | Phe | Dap | | $NH_2$ |
| Hmt | D-Lys | Phe | Arg | | $NH_2$ |
| Mmt | D-Lys | Phe | Arg | | $NH_2$ |
| Mmt | D-Orn | Phe | Arg | | $NH_2$ |
| Mmt | D-Dab | Phe | Arg | | $NH_2$ |
| Mmt | D-Dap | Phe | Arg | | $NH_2$ |
| Mmt | D-Arg | Phe | Arg | | $NH_2$ |
| Tmt | D-Lys | Phe | Arg | | $NH_2$ |
| Tmt | D-Orn | Phe | Arg | | $NH_2$ |
| Tmt | D-Dab | Phe | Arg | | $NH_2$ |
| Tmt | D-Dap | Phe | Arg | | $NH_2$ |
| Tmt | D-Arg | Phe | Arg | | $NH_2$ |
| Hmt | D-Lys | Phe | Arg | | $NH_2$ |
| Hmt | D-Orn | Phe | Arg | | $NH_2$ |
| Hmt | D-Dab | Phe | Arg | | $NH_2$ |
| Hmt | D-Dap | Phe | Arg | | $NH_2$ |
| Hmt | D-Arg | Phe | Arg | | $NH_2$ |

Dab = diaminobutyric
Dap = diaminopropionic acid
Dmt = dimethyltyrosine
Mmt = 2'-methyltyrosine
Tmt = N,2'6'-trimethyltyrosine
Hmt = 2'hydroxy,6'-methyltyrosine
dnsDap = β-dansyl-L-α,β-diaminopropionic acid
antDap = β-anthraniloyl-L-α,β-diaminopropionic acid
Bio = biotin Examples of analogs useful in the practice of the present invention that do not activate mu-opioid receptors include, but are not limited to, the aromatic-cationic peptides shown in Table 2.

TABLE 2

| Amino Acid Position 1 | Amino Acid Position 2 | Amino Acid Position 3 | Amino Acid Position 5 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |

TABLE 2-continued

| Amino Acid Position 1 | Amino Acid Position 2 | Amino Acid Position 3 | Amino Acid Position 5 | C-Terminal Modification |
|---|---|---|---|---|
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl

The amino acids of the peptides shown in table 1 and 2 may be in either the L- or the D-configuration.

Methods of Treating

The peptides described above are useful in treating any disease or condition that is associated with MPT. Such diseases and conditions include, but are not limited to, ischemia and/or reperfusion of a tissue or organ, hypoxia and any of a number of neurodegenerative diseases. Mammals in need of treatment or prevention of MPT are those mammals suffering from these diseases or conditions.

Ischemia in a tissue or organ of a mammal is a multifaceted pathological condition which is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle.

The organ affected by ischemia or hypoxia may be any organ that is subject to ischemia or hypoxia. Examples of organs affected by ischemia or hypoxia include brain, heart, kidney, and prostate. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages.

Reperfusion is the restoration of blood flow to any organ or tissue in which the flow of blood is decreased or blocked. For example, blood flow can be restored to any organ or tissue affected by ischemia or hypoxia. The restoration of blood flow (reperfusion) can occur by any method known to those in the art. For instance, reperfusion of ischemic cardiac tissues may arise from angioplasty, coronary artery bypass graft, or the use of thrombolytic drugs.

The methods of the present invention can also be used in the treatment or prophylaxis of neurodegenerative diseases associated with MPT. Neurodegenerative diseases associated with MPT include, for instance, Parkinson's disease, Alzheimer's disease, Huntington's disease and Amyotrophic Lateral Sclerosis (ALS, also known as Lou Gehrig's disease). The methods of the present invention can be used to delay the onset or slow the progression of these and other neurodegenerative diseases associated with MPT. The methods of the present invention are particularly useful in the treatment of humans suffering from the early stages of neurodegenerative diseases associated with MPT and in humans predisposed to these diseases.

The peptides useful in the present invention may also be used in preserving an organ of a mammal prior to transplantation. For example, a removed organ can be susceptible to MPT due to lack of blood flow. Therefore, the peptides can be used to prevent MPT in the removed organ.

The removed organ can be placed in a standard buffered solution, such as those commonly used in the art. For example, a removed heart can be placed in a cardioplegic solution containing the peptides described above. The concentration of peptides in the standard buffered solution can be easily determined by those skilled in the art. Such concentrations may be, for example, between about 0.1 nM to about 10 μM, preferably about 1 μM to about 10 μM.

The peptides may also be administered to a mammal taking a drug to treat a condition or disease. If a side effect of the drug includes MPT, mammals taking such drugs would greatly benefit from the peptides of the invention.

An example of a drug which induces cell toxicity by effecting MPT is the chemotherapy drug Adriamycin.

Synthesis of the Peptides

The peptides useful in the methods of the present invention may be chemically synthesized by any of the methods well known in the art. Suitable methods for synthesizing the protein include, for example those described by Stuart and Young in "Solid Phase Peptide Synthesis," Second Edition, Pierce Chemical Company (1984), and in "Solid Phase Peptide Synthesis," Methods Enzymol. 289, Academic Press, Inc, New York (1997).

Modes of Administration

The peptide useful in the methods of the present invention is administered to a mammal in an amount effective in reducing the number of mitochondria undergoing, or preventing, MPT. The effective amount is determined during pre-clinical trials and clinical trials by methods familiar to physicians and clinicians.

An effective amount of a peptide useful in the methods of the present invention, preferably in a pharmaceutical composition, may be administered to a mammalian need thereof by any of a number of well-known methods for administering pharmaceutical compounds.

The peptide may be administered systemically or locally. In one embodiment, the peptide is administered intravenously. For example, the aromaticcationic peptides useful in the methods of the present invention may be administered via rapid intravenous bolus injection. Preferably, however, the peptide is administered as a constant rate intravenous infusion.

The peptide can be injected directly into coronary artery during, for example, angioplasty or coronary bypass surgery, or applied onto coronary stents.

The peptide may also be administered orally, topically, intranasally, intramuscularly, subcutaneously, or transdermally. In a preferred embodiment, transdermal administration of the aromatic-cationic peptides by methods of the present invention is by iontophoresis, in which the charged peptide is delivered across the skin by an electric current.

Other routes of administration include intracerebroventricularly or intrathecally. Intracerebroventiculatly refers to administration into the ventricular system of the brain. Intrathecally refers to administration into the space under the arachnoid membrane of the spinal cord. Thus intracerebroventricular or intrathecal administration may be preferred for those diseases and conditions which affect the organs or tissues of the central nervous system. In a preferred embodiment, intrathecal administration is used for traumatic spinal cord injury.

The peptides useful in the methods of the invention may also be administered to mammals by sustained release, as is known in the art. Sustained release administration is a method of drug delivery to achieve a certain level of the drug over a particular period of time. The level typically is measured by serum or plasma concentration.

Any formulation known in the art of pharmacy is suitable for administration of the aromatic-cationic peptides useful in the methods of the present invention. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the aromatic-cationic peptides useful in the methods of the present inventions may utilize conventional diluents, carriers, or excipients etc., such as are known in the art can be employed to deliver the peptides. For example, the formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the peptide.

The surfactant is preferably a nonionic surfactant, such as a polysorbate. Some examples of suitable surfactants include Tween20, Tween80; a polyethylene glycolor a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the peptides useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits In a preferred embodiment, the mammal is a human.

EXAMPLES

Example 1

[Dmt$^1$]DALDA Penetrates Cell Membrane

The cellular uptake of [$^3$H][Dmt$^1$]DALDA was studied using a human intestinal epithelial cell line (Caco-2), and confirmed with SH-SY5Y (human neuroblastoma cell), HEK293 (human embryonic kidney cell) and CRFK cells (kidney epithelial cell). Monolayers of cells were grown on 12-well plates (5×10$^5$ cells/well) coated with collagen for 3 days. On day 4, cells were washed twice with pre-wanned HBSS, and then incubated with 0.2 ml of HBSS containing either 250 nM [$^3$H][Dmt$^1$]DALDA at 37° C. or 4° C. for various times up to 1 h.

[$^3$H][Dmt$^1$]DALDA was observed in cell lysate as early as 5 min, and steady state levels were achieved by 30 min. The total amount of [$^3$H][Dmt$^1$]DALDA recovered in the cell lysate after 1 h incubation represented about 1% of the total drug. The uptake of [$^3$H][Dmt$^1$]DALDA was slower at 4° C. compared to 37° C., but reached 76.5% by 45 min and 86.3% by 1 h. The internalization of [$^3$H][Dmt$^1$]DALDA was not limited to Caco-2 cells, but was also observed in SH-SY5Y, HEK293 and CRFK cells. The intracellular concentration of [Dmt$^1$]DALDA was estimated to be approximately 50 times higher than extracellular concentration.

In a separate experiment, cells were incubated with a range of [Dmt$^1$]DALDA concentrations (1 μM-3 mM) for 1 h at 37° C. At the end of the incubation period, cells were washed 4 times with HBSS, and 0.2 ml of 0.1N NaOH with 1% SDS was added to each well. The cell contents were then transferred to scintillation vials and radioactivity counted. To distinguish between internalized radioactivity from surface-associated radioactivity, an acid-wash step was included. Prior to cell lysis, cells were incubated with 0.2 ml of 0.2 M acetic acid/0.05 M NaCl for 5 min on ice.

The uptake of [Dmt$^1$]DALDA into Caco-2 cells was confirmed by confocal laser scanning microscopy (CLSM) using a fluorescent analog of [Dmt$^1$]DALDA (Dmt-D-Arg-Phe-dnsDap-NH$_2$; where dnsDap=β-dansyl-1-α,β-diaminopropionic acid). Cells were grown as described above and were plated on (35 mm) glass bottom dishes (MatTek Corp., Ashland, Mass.) for 2 days. The medium was then removed and cells were incubated with 1 ml of HBSS containing 0.1 μM to 1.0 μM of the fluorescent peptide analog at 37° C. for 1 h. Cells were then washed three times with ice-cold HBSS and covered with 200 μl of PBS, and microscopy was performed within 10 min at room temperature using a Nikon confocal laser scanning microscope with a C-Apochromat 63×/1.2 W corr objective. Excitation was performed at 340 nm by means of a UV laser, and emission was measured at 520 nm. For optical sectioning in z-direction, 5-10 frames with 2.0 μm were made.

CLSM confirmed the uptake of fluorescent Dmt-D-Arg-Phe-dnsDap-NH$_2$ into Caco-2 cells after incubation with 0.1 μM [Dmt$^1$,DnsDap$^4$]DALDA for 1 h at 37° C. The uptake of the fluorescent peptide was similar at 37° C. and 4° C. The fluorescence appeared diffuse throughout the cytoplasm but was completely excluded from the nucleus.

Example 2

Targeting of [Dmt$^1$]DALDA to Mitochondria

To examine the subcellular distribution of [Dmt$^1$]DALDA, the fluorescent analog, [Dmt$^1$, AtnDap$^4$]DALDA (Dmt-D-Arg-Phe-atnDap-NH$_2$; where atn=β-anthraniloyl-1-α,β-diamino-propionic acid), was prepared. The analog contained β-anthraniloyl-1-α,β-diaminopropionic acid in place of the lysine reside at position 4. The cells were grown as described in Example 1 and were plated on (35 mm) glass bottom dishes (MatTek Corp., Ashland, Mass.) for 2 days. The medium was then removed and cells were incubated with 1 ml of HBSS containing 0.1 μM of [Dmt$^1$, AtnDap$^4$]DALDA at 37° C. for 15 min to 1 h.

Cells were also incubated with tetramethylrhodamine methyl ester (TMRM, 25 nM), a dye for staining mitochondria, for 15 min at 37° C. Cells were then washed three times with ice-cold HBSS and covered with 200 μl of PBS, and microscopy was performed within 10 min at room temperature using a Nikon confocal laser scanning microscope with a C-Apochromat 63×/1.2 W corr objective.

For [Dmt$^1$, AtnDap$^4$]DALDA, excitation was performed at 350 nm by means of a UV laser, and emission was measured at 520 nm. For TMRM, excitation was performed at 536 nm, and emission was measured at 560 nm.

CLSM showed the uptake of fluorescent [Dmt$^1$, AtnDap$^4$] DALDA into Caco-2 cells after incubation for as little as 15 min at 37° C. The uptake of dye was completely excluded from the nucleus, but the blue dye showed a streaky distribution within the cytoplasm. Mitochondria were labeled red with TMRM. The distribution of [Dmt$^1$, AtnDap$^4$]DALDA to mitochondria was demonstrated by the overlap of the [Dmt$^1$, AtnDap$^4$]DALDA distribution and the TMRM distribution.

Example 3

Uptake of [Dmt$^1$]DALDA into Mitochondria

To isolate mitochondria from mouse liver, mice were sacrificed by decapitation. The liver was removed and rapidly placed into chilled liver homogenization medium. The liver was finely minced using scissors and then homogenized by hand using a glass homogenizer.

The homogenate was centrifuged for 10 min at 1000×g at 4° C. The supernatant was aspirated and transferred to polycarbonate tubes and centrifuged again for 10 min. at 3000×g, 4° C. The resulting supernatant was removed, and the fatty lipids on the side-wall of the tube were carefully wiped off.

The pellet was resuspended in liver homogenate medium and the homogenization repeated twice. The final purified mitochondrial pellet was resuspended in medium. Protein concentration in the mitochondrial preparation was determined by the Bradford procedure.

Approximately 1.5 mg mitochondria in 400 μl buffer was incubated with [$^3$H][Dmt$^1$]DALDA for 5-30 min at 37° C. The mitochondria were then centrifuged down and the amount of radioactivity determined in the mitochondrial fraction and buffer fraction. Assuming a mitochondrial matrix volume of 0.7 μl/mg protein (Lim et al., *J Physiol*, 545:961-974, 2002), the concentration of [$^3$H][Dmt$^1$]DALDA in mitochondria was found to be 200 times higher than in the buffer. Thus [Dmt$^1$]DALDA is concentrated in mitochondria.

Based on these data, the concentration of [Dmt$^1$]DALDA in mitochondria when the isolated guinea pig hearts were perfused with [Dmt$^1$]DALDA can be estimated:

| | |
|---|---|
| Concentration of [Dmt$^1$]DALDA in coronary perfusate | 0.1 μM |
| Concentration of [Dmt$^1$]DALDA in myocyte | 5 μM |
| Concentration of [Dmt$^1$]DALDA in mitochondria | 1.0 mM |

Example 4

Accumulation of [Dmt$^1$]DALDA by Isolated Mitochondria (FIG. 1)

To further demonstrate that [Dmt$^1$]DALDA is selectively distributed to mitochondria, we examined the uptake of [Dmt$^1$, AtnDap$^4$]DALDA and [$^3$H][Dmt$^1$]DALDA into isolated mouse liver mitochondria. The rapid uptake of [Dmt$^1$, AtnDap$^4$]DALDA was observed as immediate quenching of its fluorescence upon addition of mitochondria (FIG. 1 A). Pretreatment of mitochondria with FCCP (carbonyl cyanide p-(trifluoromethoxy)-phenylhydrazone), an uncoupler that results in immediate depolarization of mitochondria, only reduced [Dmt$^1$, AtnDap$^4$]DALDA uptake by <20%. Thus uptake of [Dmt$^1$, AtnDap$^4$]DALDA was not potential-dependent.

Figure 1B:
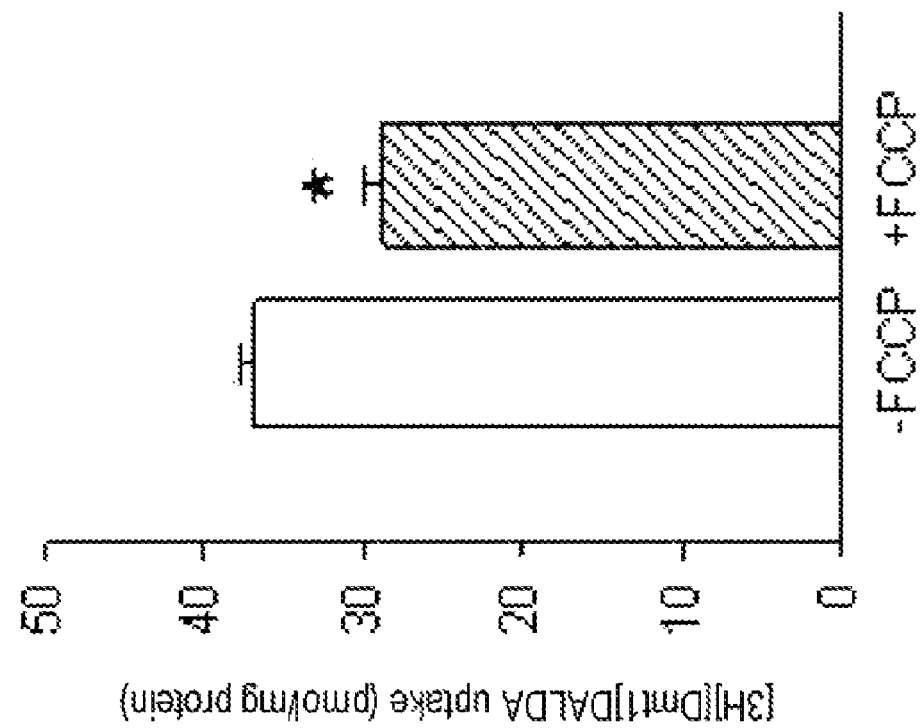
(FIG. 1B) Isolated mitochondria were incubated with [$^3$H]SS-02 at 37° C. for 2 min. Uptake was stopped by centrifugation (16000×g) for 5 min at 4° C., and radioactivity determined in the pellet. Pretreatment of mitochondria with FCCP inhibited [$^3$H]SS-02 uptake by ~20%. Data are shown as mean±s.e.; n=3. *, $P<0.05$ by Student's t-test.

To confirm that the mitochondrial targeting was not an artifact of the fluorophore, we also examined mitochondrial uptake of [$^3$H][Dmt$^1$]DALDA. Isolated mitochondria were incubated with [$^3$H][Dmt$^1$]DALDA and radioactivity determined in the mitochondrial pellet and supernatant. The amount of radioactivity in the pellet did not change from 2 min to 8 min. Treatment of mitochondria with FCCP only decreased the amount of [$^3$H][Dmt$^1$]DALDA associated with the mitochondrial pellet by ~20% (FIG. 1B).

Figure 1C:
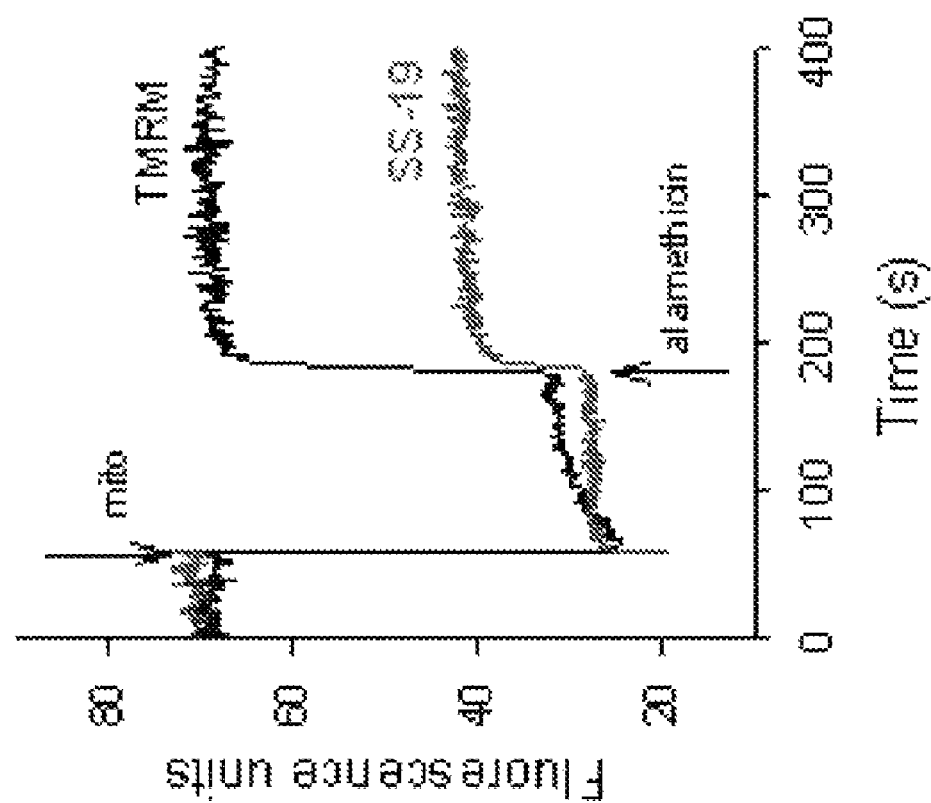
(FIG. 1C) Uptake of TMRM by isolated mitochondria is lost upon mitochondrial swelling induced by alamethicin, while uptake of SS-19 is retained to a large extent. Black line, TMRM; red line, SS-19.

The minimal effect of FCCP on [Dmt$^1$]DALDA uptake suggested that [Dmt$^1$]DALDA was likely to be associated with mitochondrial membranes or in the intermembrane space rather than in the matrix. We next examined the effect of mitochondrial swelling on the accumulation of [Dmt$^1$, AtnDap$^4$]DALDA in mitochondria by using alamethicin to induce swelling and rupture of the outer membrane. Unlike TMRM, the uptake of [Dmt$^1$, AtnDap$^4$]DALDA was only partially reversed by mitochondrial swelling (FIG. 1C). Thus, [Dmt$^1$]DALDA is associated with mitochondrial membranes.

Example 5

Figure 1D:
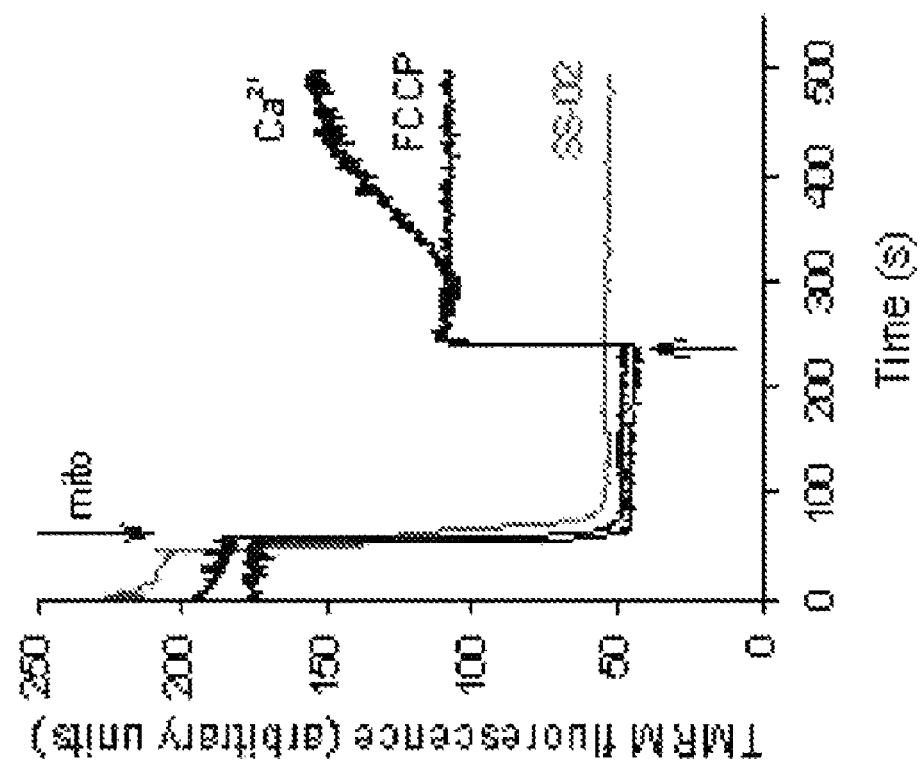
(FIG. 1D) Addition of SS-02 (200 µM) to isolated mitochondria did not alter mitochondrial potential, as measured by TMRM fluorescence. Addition of FCCP (1.5 µM) caused immediate depolarization while Ca$^{2+}$ (150 µM) resulted in depolarization and progressive onset of MPT.

[Dmt$^1$]DALDA does not Alter Mitochondrial Respiration or Potential (FIG. 1*d*)

The accumulation of [Dmt$^1$]DALDA in mitochondria did not alter mitochondrial function. Incubating isolated mouse liver mitochondria with 100 μM [Dmt$^1$]DALDA did not alter oxygen consumption during state 3 or state 4, or the respiratory ratio (state 3/state 4) (6.2 versus 6.0). Mitochondrial membrane potential was measured using TMRM (FIG. 1D) Addition of mitochondria resulted in immediate quenching of the TMRM signal which was readily reversed by the addition of FCCP, indicating mitochondrial depolarization. The addition of Ca$^{2+}$ (150 μM) resulted in immediate depolarization followed by progressive loss of quenching indicative of MPT. Addition of [Dmt$^1$]DALDA alone, even at 200 μM, did not cause mitochondrial depolarization or MPT.

Example 6

Figure 2A:
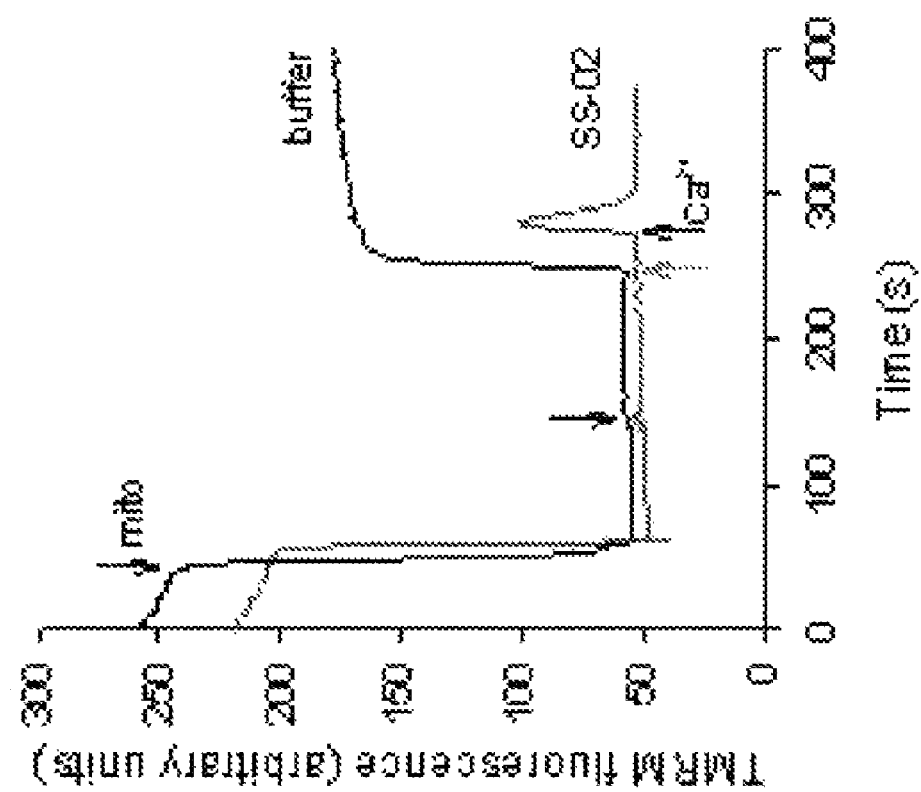
(FIG. 2A) Pretreatment of isolated mitochondria with 10 µM SS-02 (addition indicated by down arrow) prevented onset of MPT caused by Ca$^{2+}$ overload (up arrow). Black line, buffer; red line, SS-02 (FIG. 2B) Pretreatment of isolated mitochondria with SS-02 increased mitochondrial tolerance of multiple Ca$^{2+}$ additions prior to onset of MPT. Arrow indicates addition of buffer or SS-02. Line 1, buffer; line 2, 50 µM SS-02; line 3, 100 µM SS-02.

[Dmt$^1$]DALDA Protects Against MPT Induced by Ca$^{2+}$ and 3-Nitropropionic Acid (FIG. 2)

Figure 2B:
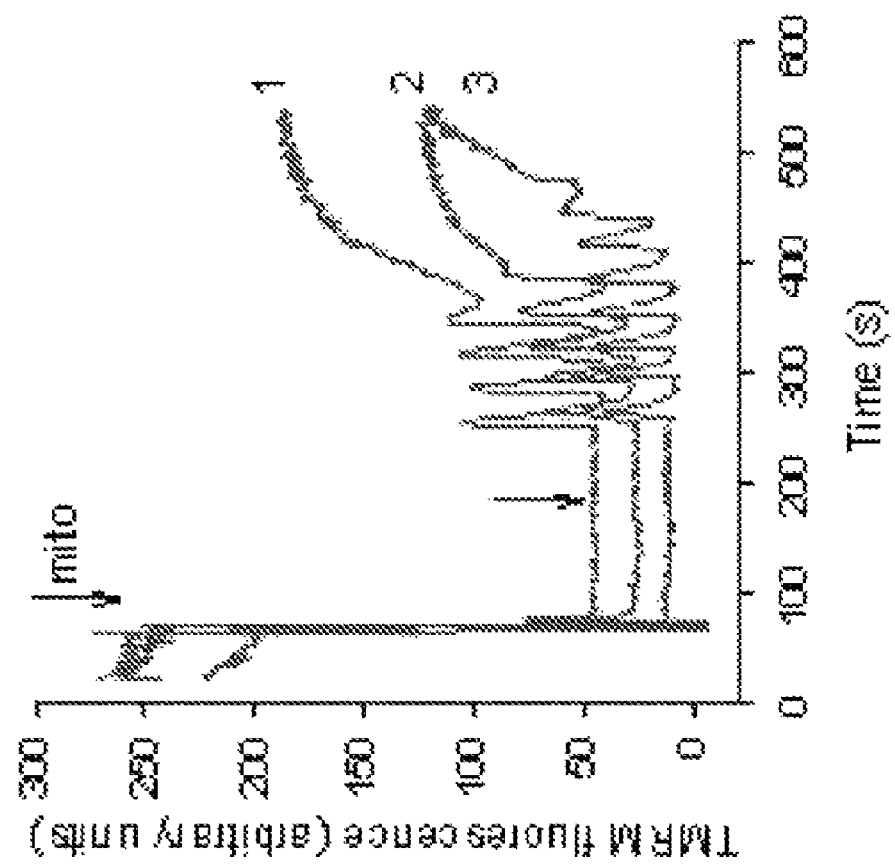
FIG. 2. [Dmt$^1$]DALDA (SS-02) protects against mitochondrial permeability transition (MPT) induced by Ca$^{2+}$ overload and 3-nitroproprionic acid (3NP).
(FIG. 2C) SS-02 dose-dependently delayed the onset of MPT caused by 1 mM 3NP. Arrow indicates addition of buffer or SS-02. Line 1, buffer; line 2, 0.5 µM SS-02; line 3, 5 µM SS-02; line 4, 50 µM SS-02.

In addition to having no direct effect on mitochondrial potential, [Dmt$^1$]DALDA was able to protect against MPT induced by Ca$^{2+}$ overload. Pretreatment of isolated mitochondria with [Dmt$^1$]DALDA (10 μM) for 2 min prior to addition of Ca$^{2+}$ resulted only in transient depolarization and prevented onset of MPT (FIG. 2A), [Dmt$^1$]DALDA dose-dependently increased the tolerance of mitochondria to cumulative Ca$^{2+}$ challenges. FIG. 2B shows that [Dmt$^1$]DALDA increased the number of Ca$^{2+}$ additions that isolated mitochondria could tolerate prior to MPT.

Figure 2C:
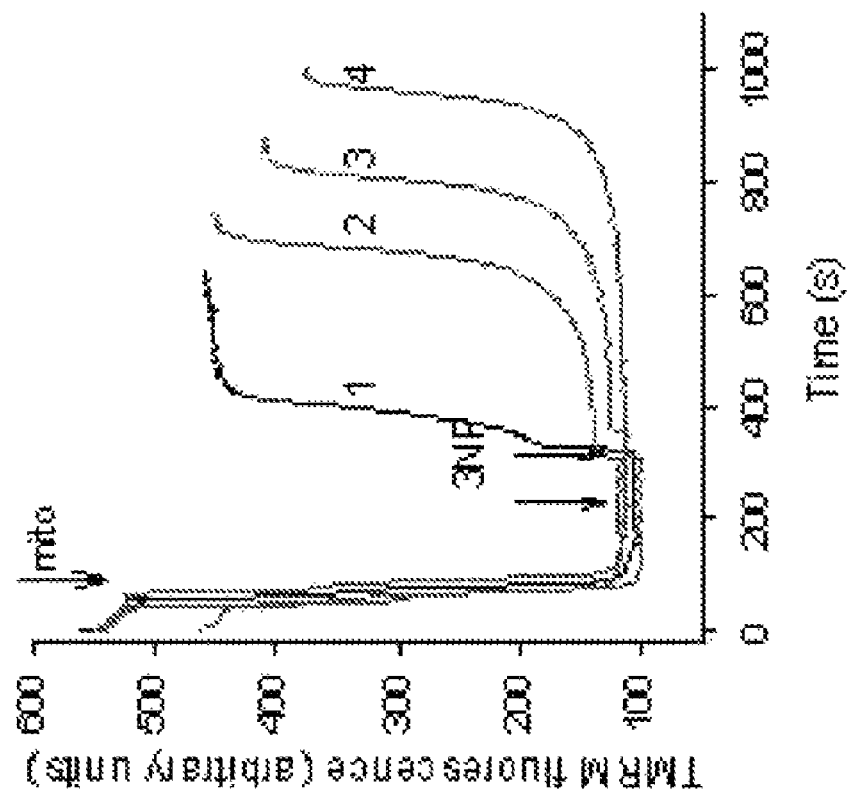

3-Nitropropionic acid (3NP) is an irreversible inhibitor of succinate dehydrogenase in complex II of the electron transport chain. Addition of 3NP (1 mM) to isolated mitochondria caused dissipation of mitochondrial potential and onset of MPT (FIG. 2C). Pretreatment of mitochondria with [Dmt$^1$]DALDA dose-dependently delayed the onset of MPT induced by 3NP (FIG. 2C).

To demonstrate that [Dmt$^1$]DALDA can penetrate cell membranes and protect against mitochondrial depolarization elicited by 3NP, Caco-2 cells were treated with 3NP (10 mM) in the absence or presence of [Dmt$^1$]DALDA (0.1 μM) for 4 h, and then incubated with TMRM and examined under LSCM. In control cells, the mitochondria are clearly visualized as fine streaks throughout the cytoplasm. In cells treated with 3NP, the TMRM fluorescence was much reduced, suggesting generalized depolarization. In contrast, concurrent treatment with [Dmt$^1$]DALDA protected against mitochondrial depolarization caused by 3NP.

Example 7

[Dmt$^1$]DALDA Protects Against Mitochondrial Swelling and Cytochrome c Release

Figure 3A:
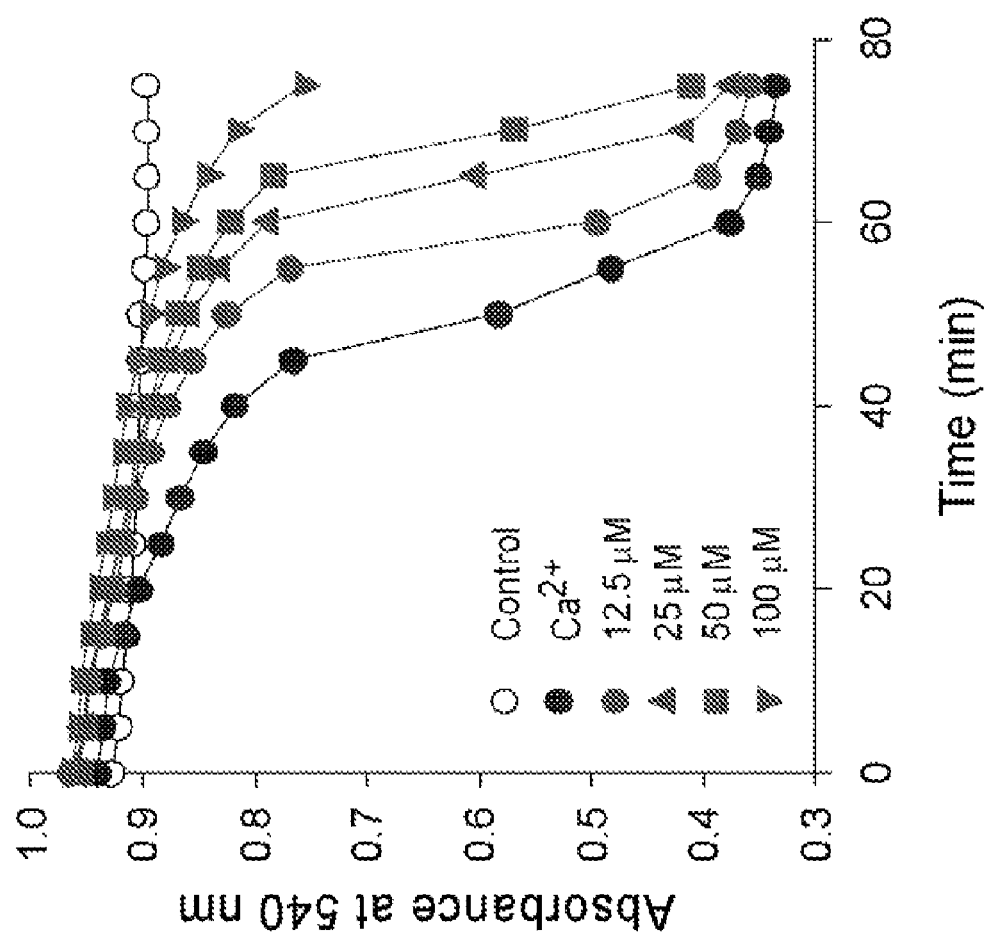
(FIG. 3A) Pretreatment of isolated mitochondria with SS-02 dose dependently inhibited mitochondrial swelling induced by 200 µM Ca$^{2+}$ in a dose-dependent manner. Swelling was measured by absorbance at 540 nm.
Figure 3B:
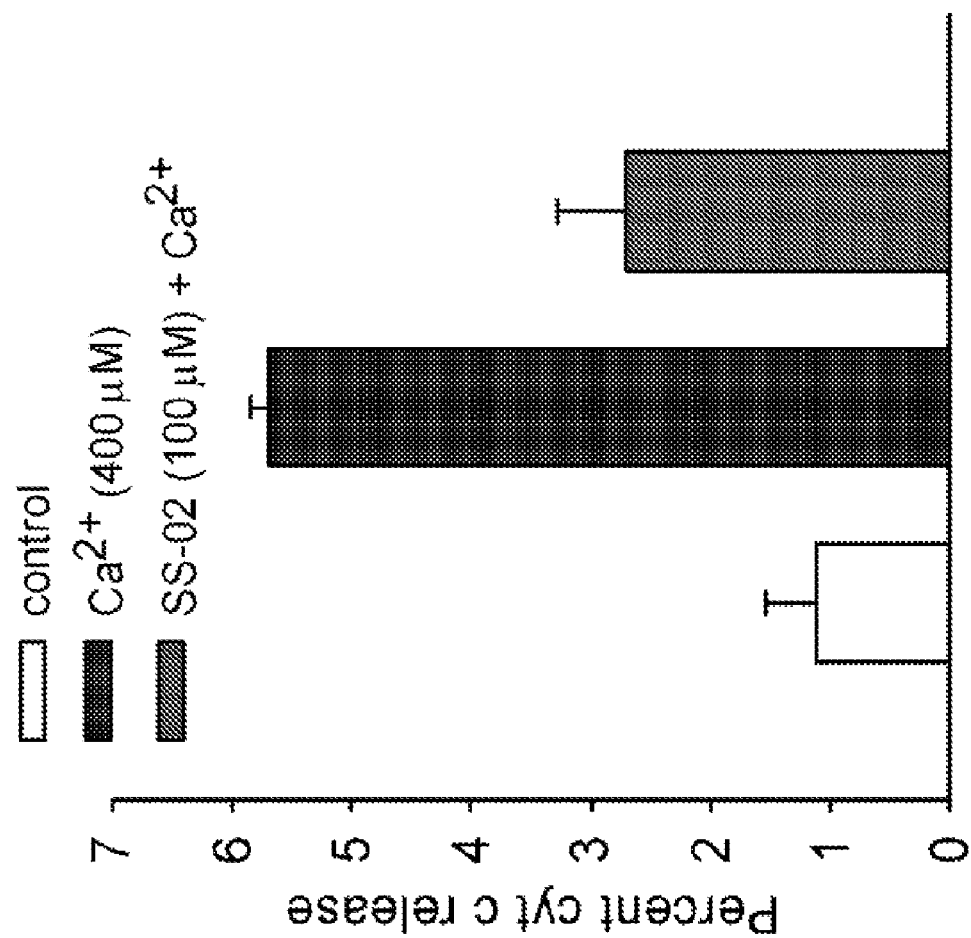
(FIG. 3B) SS-02 inhibited Ca$^{2+}$-induced release of cytochrome c from isolated mitochondria. The amount of cytochrome c released was expressed as percent of total cytochrome c in mitochondria. Data are presented as mean±s.e., n=3.
Figure 3C:
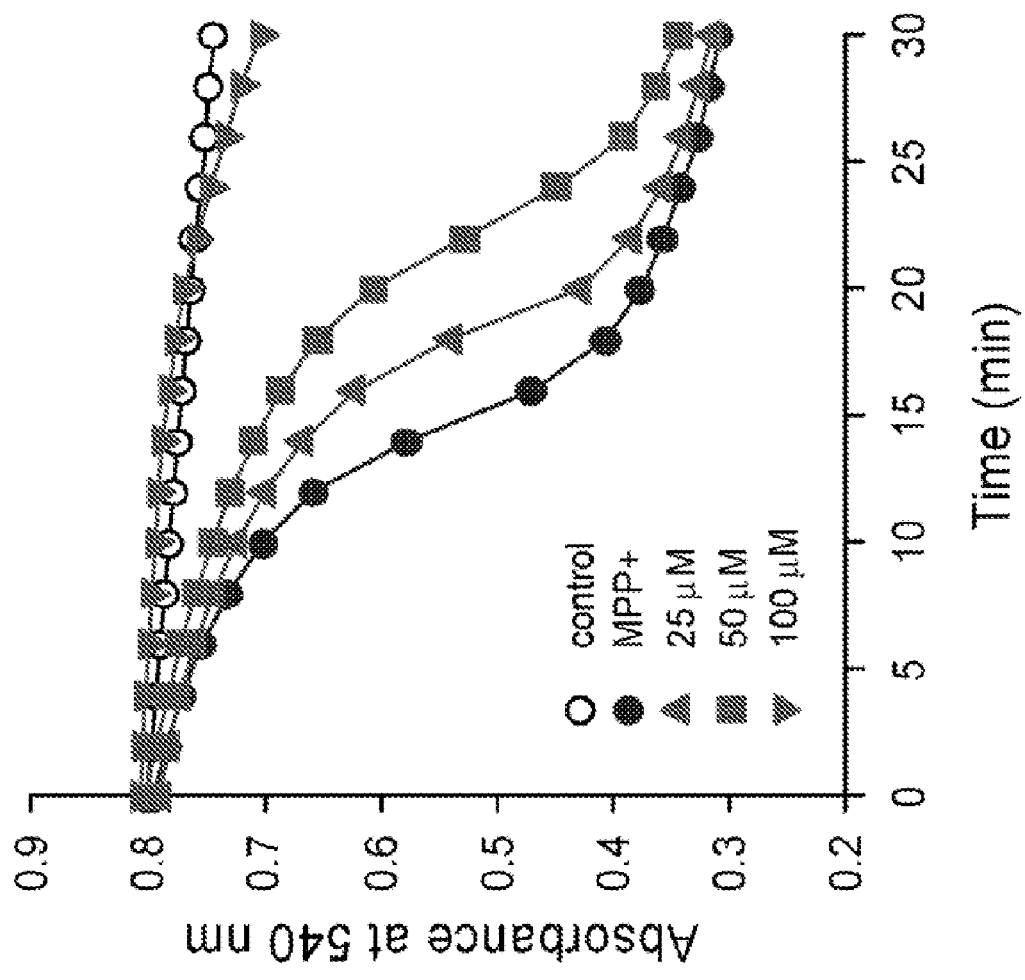
(FIG. 3C) SS-02 also inhibited mitochondrial swelling induced by MPP$^+$ (300 µM).

MPT pore opening results in mitochondrial swelling. We examined the effects of [Dmt$^1$]DALDA on mitochondrial swelling by measuring reduction in absorbance at 540 nm ($A_{540}$). The mitochondrial suspension was then centrifuged and cytochrome c in the mitochondrial pellet and supernatant determined by a commercially-available ELISA kit. Pretreatment of isolated mitochondria with SS-02 inhibited swelling (FIG. 3A) and cytochrome c release (FIG. 3B) induced by Ca$^{2+}$ overload. Besides preventing MPT induced by Ca$^{2+}$ overload, SS-02 also prevented mitochondrial swelling induced by MPP$^+$ (1-methyl-4-phenylpyridium ion), an inhibitor of complex I of the mitochondrial electron transport chain (FIG. 3C).

Example 8

Figure 4A:
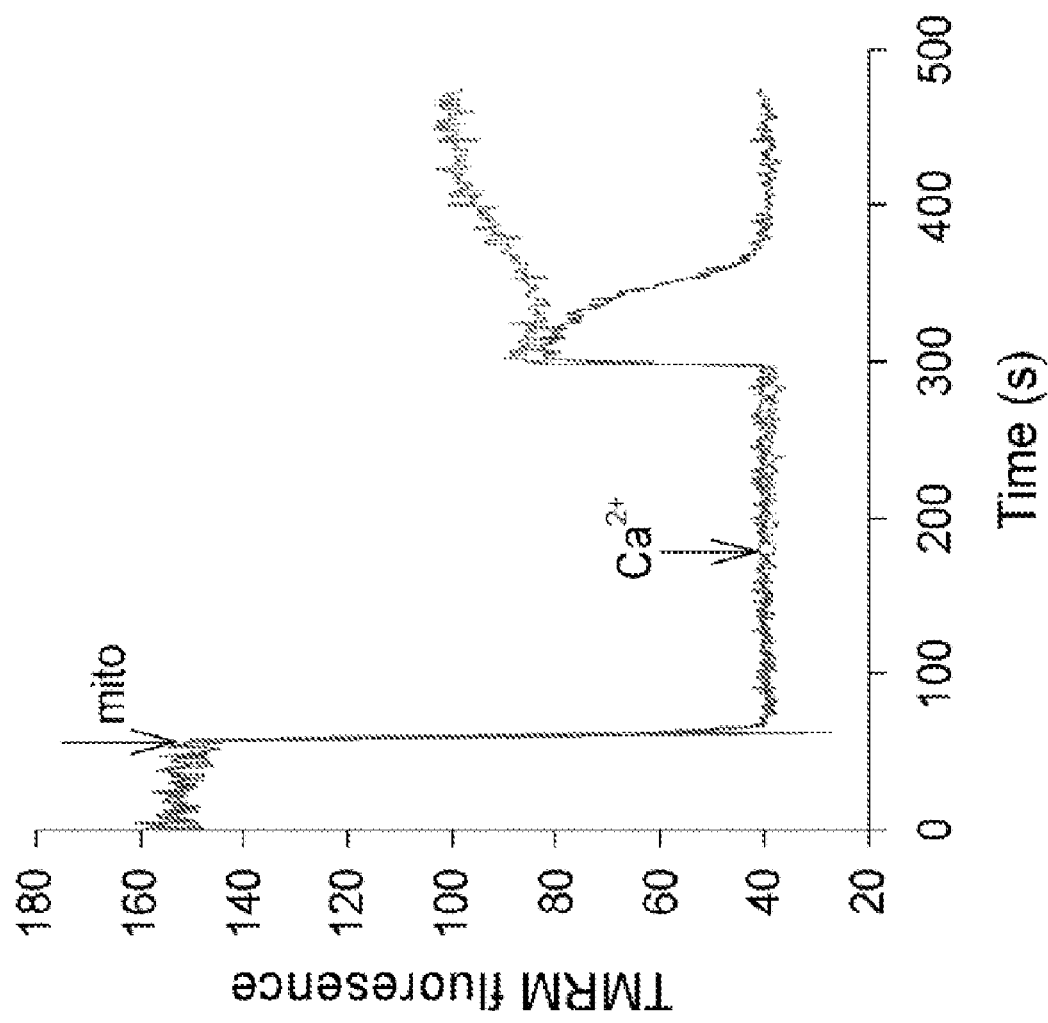
(FIG. 4A) Pretreatment of isolated mitochondria with SS-31 (10 µM) prevents onset of MPT induced by Ca$^{2+}$. Gray line, buffer; red line, SS-31.
Figure 4B:
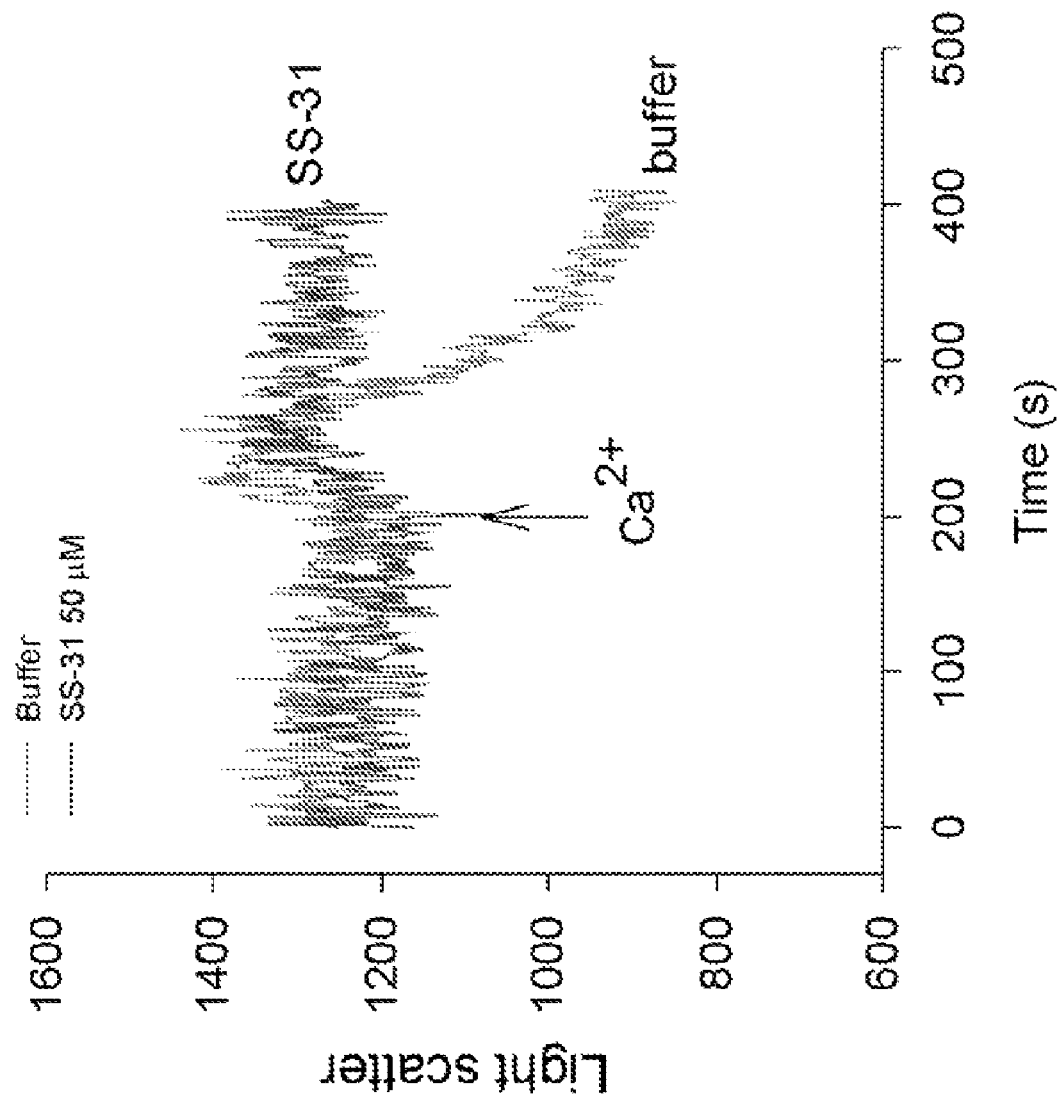
(FIG. 4B) Pretreatment of mitochondria with SS-31 (50 µM) inhibited mitochondrial swelling induced by 200 mM Ca$^{2+}$. Swelling was measured by light scattering measured at 570 nm.
Figure 4C:
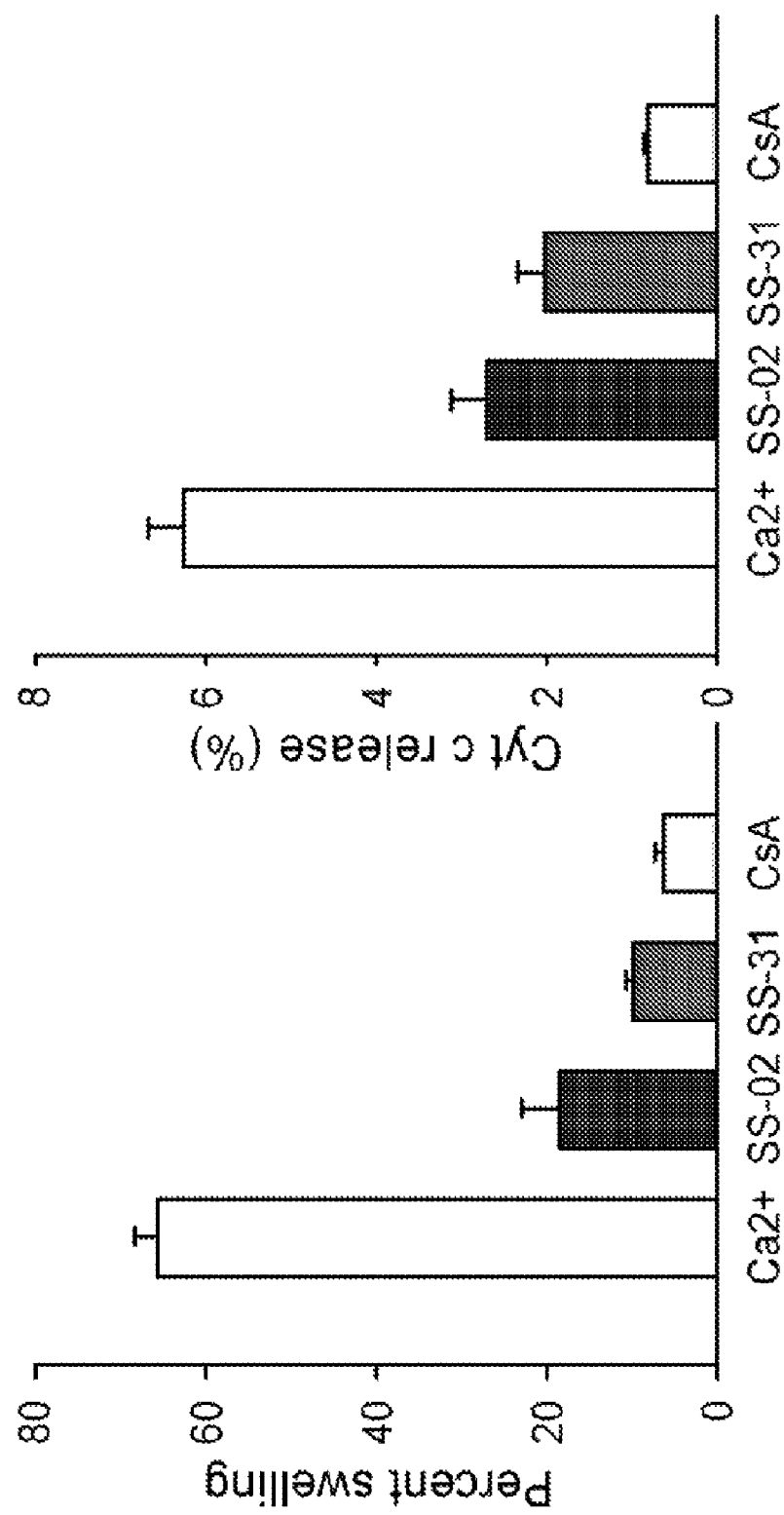
(FIG. 4C). Comparison of SS-02 and SS-31 with cyclosporine (CsA) in inhibiting mitochondrial swelling and cytochrome c release induced by Ca$^{2+}$, The amount of cytochrome c released was expressed as percent of total cytochrome c in mitochondria. Data are presented as mean±s.e., n=3.

D-Arg-Dmt-Lys-Phe-NH$_2$ (SS-31) can Protect Against MPT, Mitochondrial Swelling and Cytochrome c Release The non-opioid peptide SS-31 has the same ability to protect against MPT (FIG. 4A), mitochondrial swelling (FIG. 4B), and cytochrome c release (FIG. 4C), induced by Ca$^{2+}$. The methods for study are as described above for SS-02. In this example, mitochondrial swelling was measured using light scattering monitored at 570 nm.

Example 9

[Dmt$^1$]DALDA (SS-02) and D-Arg-Dmt-Lys-Phe-NH$_2$ (SS-31) Protects Against Ischemia-Reperfusion-Induced Myocardial Stunning Guinea pig hearts were rapidly isolated, and the aorta was cannulated in situ and perfused in a retrograde fashion with an oxygenated Krebs-Henseleit solution (pH 7.4) at 34° C. The heart was then excised, mounted on a modified Langendorff perfusion apparatus, and perfused at constant pressure (40 cm H$_2$O). Contractile force was measured with a small hook inserted into the apex of the left ventricle and the silk ligature tightly connected to a force-displacement transducer. Coronary flow was measured by timed collection of pulmonary artery effluent.

Hearts were perfused with buffer, [Dmt$^1$]DALDA (SS-02) (100 nM) or D-Arg-Dmt-Lys-Phe-NH$_2$ (SS-31) (1 nM) for 30 min and then subjected to 30 min of global ischemia. Reperfusion was carried out with the same solution used prior to ischemia.

Figure 5:
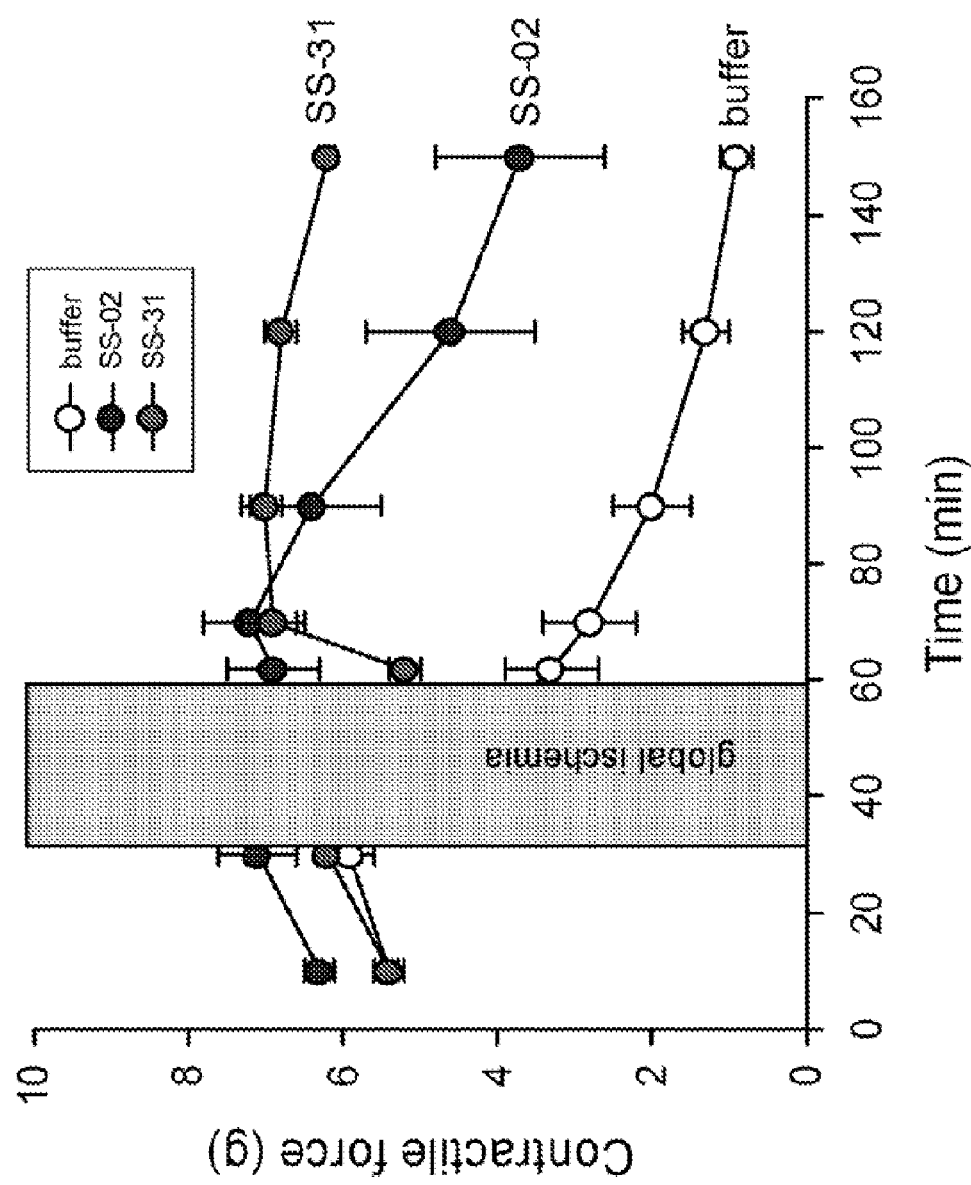
FIG. 5. [Dmt$^1$]DALDA (SS-02) and D-Arg-Dmt-Lys-Phe-NH$_2$ (SS-31) protects myocardial contractile force during ischemia-reperfusion in the isolated perfused guinea pig heart. Hearts were perfused with buffer or buffer containing SS-02 (100 nM) or SS-31 (1 nM) for 30 min and then subjected to 30-min global ischemia. Reperfusion was carried out using the same perfusion solution. Significant differences were found among the three treatment groups (2-way ANOVA, $P<0.001$).

Two-way ANOVA revealed significant differences in contractile force (P<0.001), heart rate (P=0.003), and coronary flow (P<0.001) among the three treatment groups. In the buffer group, contractile force was significantly lower during reperfusion compared with before ischemia (FIG. 5). Both SS-02 and SS-31 treated hearts tolerated ischemia much better than buffer-treated hearts (FIG. 5). In particular, SS-31 provided complete inhibition of cardiac stunning. In addition, coronary flow is well-sustained throughout reperfusion and there was no decrease in heart rate.

Example 10

[Dmt$^1$]DALDA (SS-02) Enhances Organ Preservation

For heart transplantation, the donor heart is preserved in a cardioplegic solution during transport. The preservation solution contains high potassium which effectively stops the heart from beating and conserve energy. However, the survival time of the isolated heart is still quite limited.

We examined whether [Dmt$^1$]DALDA prolongs survival of organs. In this study, [Dmt$^1$]DALDA was added to a commonly used cardioplegic solution (St. Thomas) to determine whether [[Dmt$^1$]DALDA enhances survival of the heart after prolonged ischemia (model of ex vivo organ survival).

Isolated guinea pig hearts were perfused in a retrograde fashion with an oxygenated Krebs-Henseleit solution at 34° C. After 30 min. of stabilization, the hearts were perfused with a cardioplegic solution CPS (St. Tohomas) with or without [Dmt$^1$]DALDA at 100 nM for 3 min. Global ischemia was then induced by complete interruption of coronary perfusion for 90 min. Reperfusion was subsequently carried out for 60 min. with oxygenated Krebs-Henseleit solution. Contractile force, heart rate and coronary flow were monitored continuously throughout the experiment.

Figure 6:
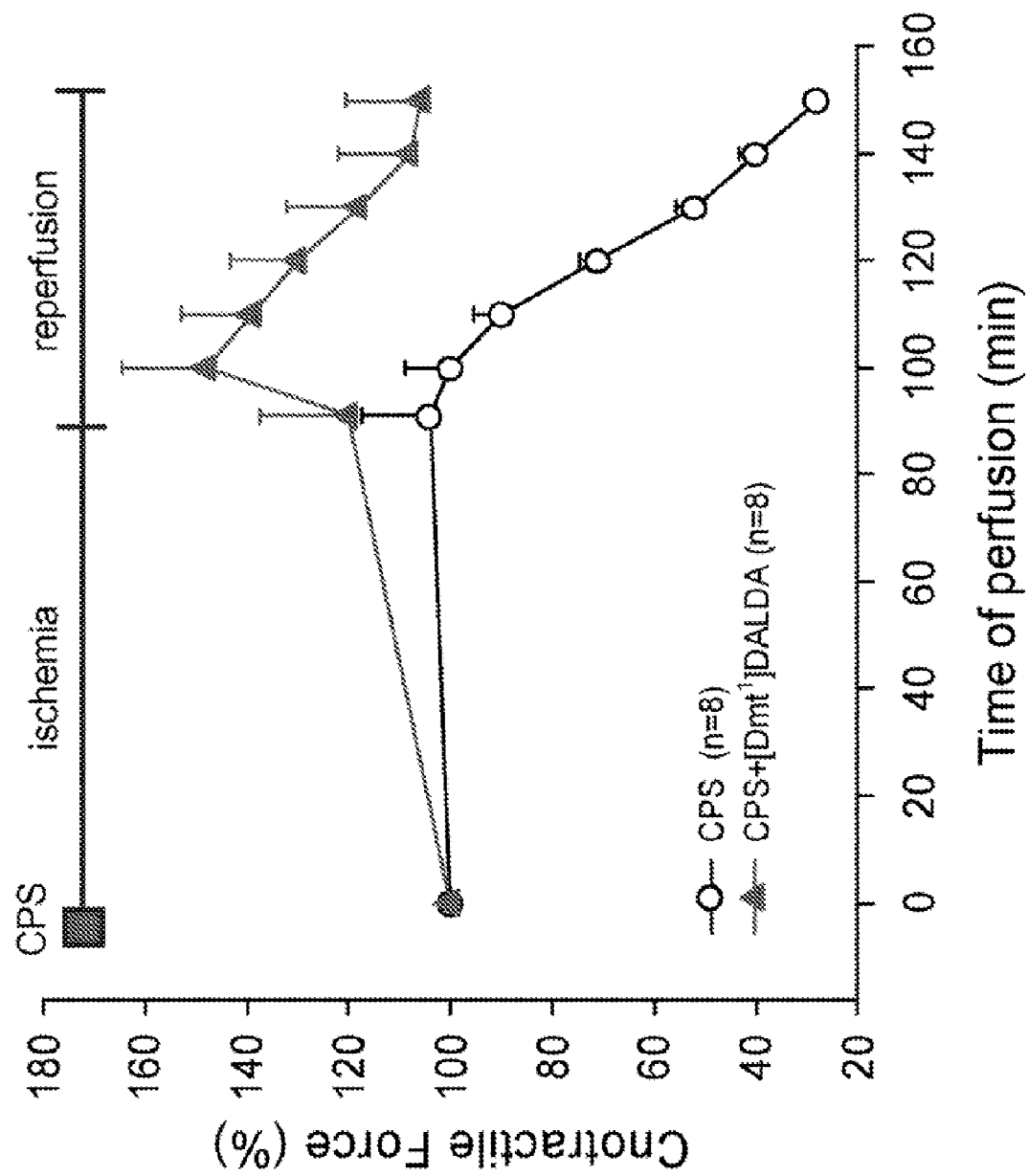
FIG. 6. Addition of [Dmt$^1$]DALDA to cardioplegic solution significantly enhanced contractile function after prolonged ischemia in the isolated perfused guinea pig heart. After 30 min stabilization, hearts were perfused with St. Thomas cardioplegic solution (CPS) or CPS containing [Dmt$^1$]DALDA at 100 µm for 3 min. Global ischemia was then induced by complete interruption of coronary perfusion for 90 min. Reperfusion was subsequently carried out for 60 min with oxygenated Krebs-Henseleit solution. Post-ischemic contractile force was significantly improved in the group receiving [Dmt$^1$]DALDA ($P<0.001$).

The addition of [Dmt$^1$]DALDA to cardioplegic solution significantly enhanced contractile function (FIG. 6) after prolonged ischemia.

Example 11

Figure 7:
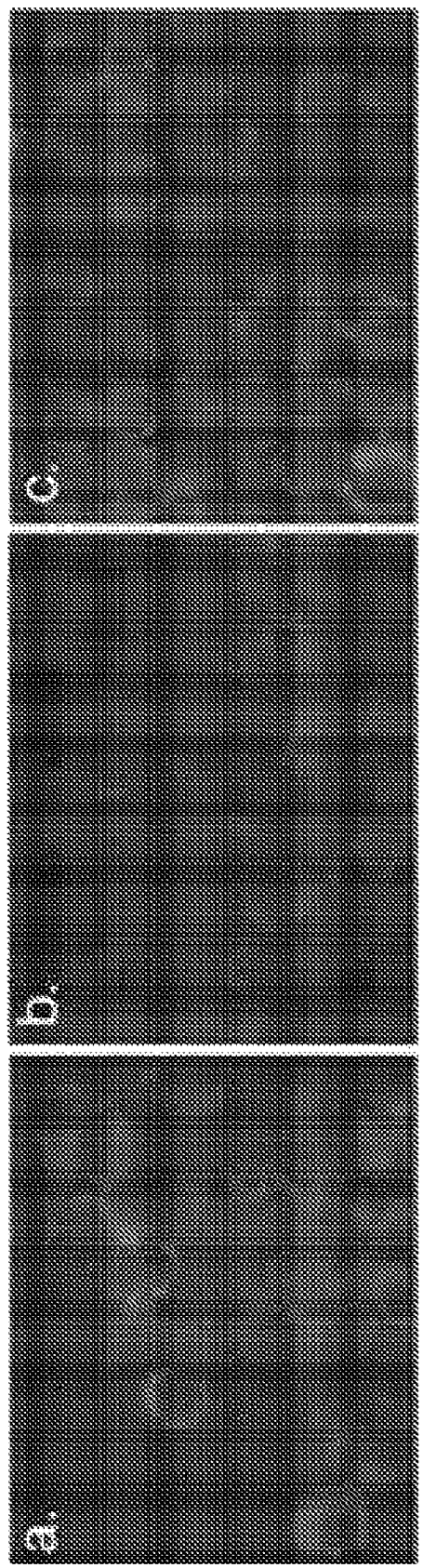
FIG. 7. SS-31 protected against tBHP-induced mitochondrial depolarization and viability. N$_2$A cells were plated in glass bottom dishes and treated with (A) control, or with (B) 50 µM tBHP, alone or with (e) 1 nM SS-31, for 6 hours. Cells were loaded with TMRM (20 nM) and imaged by confocal laser scanning microscopy using ex/em of 552/570 nm.

D-Arg-Dmt-Lys-Phe-NH$_2$ (SS-31) Prevented tBHP-Induced Mitochondrial Depolarization To investigate whether SS-31 prevents mitochondria) depolarization caused by tBHP, N2A cells were treated with 50 µM tBHP for 6 h. Treatment with tBHP resulted in a dramatic loss of mitochondrial potential. Fluorescence intensity of TMRM (red), a cationic indicator that is taken up into mitochondria in a potential dependent manner, was significantly lower in cells treated with 50 µM tBHP (FIG. 7B), and this was completely blocked by concurrent treatment with 1 nM SS-31 (FIG. 7C).

Example 12

D-Arg-Dmt-Lys-Phe-NH$_2$ (SS-31) and Phe-D-Arg-Phe-Lys-NH$_2$ (SS-20) Prevents Myocardial Infarction in Rats Methods
Infarction/Reperfusion Adult male Sprague-Dawley rats (F344 strain, National Institute of Aging, maintained by Harian Sprague-Dawley Inc.), weighting between 285 and 425 gm, were used. Twenty-four rats (n=8/group) were randomly assigned to one of three groups: (1) Control group was given 0.4 ml of saline as an intra-peritoneal (IP) injection 30 minutes before the ligation of left anterior descending coronary artery, followed by same IP dose injection 5 minutes before reperfusion; (2) SS-31 group was treated with SS-31 (3 mg/kg dissolved in 0.4 ml of saline) as an IP injection 30 minutes before the ligation followed by same IP dose injection as maintenance 5 minutes before reperfusion; and (3) SS-20 group was treated with SS-20 (3 mg/kg dissolved in 0.4 ml of saline) as an IP injection 30 minutes before the ligation followed by same dose IP injection as maintenance just 5 minutes before reperfusion. Also, Sham-operated rats (n=3) were used to account for possible effects related to the surgical protocol. All procedures were performed in a blinded manner, with the groups assigned letters and their identities unknown to the operators. Likewise, the two independent investigators analyzing the data were blind to the treatment assignments.

After anesthesia with ketamine (90 mg/kg IP) and xylazine (4 mg/kg IP), a tracheotomy was performed, and the rat was intubated with polyethylene tube and ventilated (Harvard Rodent Ventilator model 683) with room air and a tidal volume of 0.65 ml/100 gm of body weight at 90 breaths per minute. Body temperature was maintained at 37° C. by using a heated operating table. The internal jugular vein was surgically exposed and a polyethylene tube was inserted for Evans blue dye solution injection. Peripheral limb electrodes were inserted subcutaneously and electrocardiogram was monitored throughout the procedure.

Figure 8:
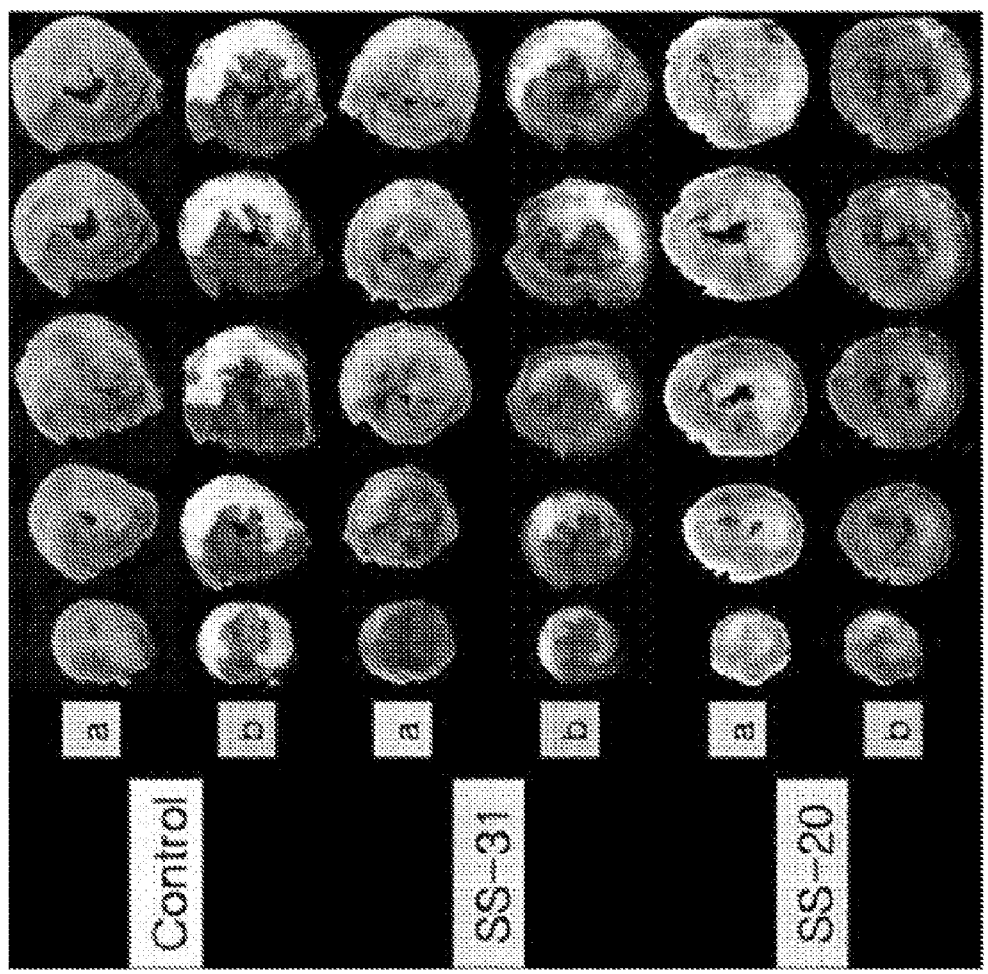
FIG. 8. Representative rat heart slices stained; (a) is myocardial ischemia area at risk, as determined by Evans blue dye (unstained by blue dye), and (b) is infarct myocardium as determined by TTC staining and formalin fixation (the pink and white areas unstained by TTC).
Figure 9:
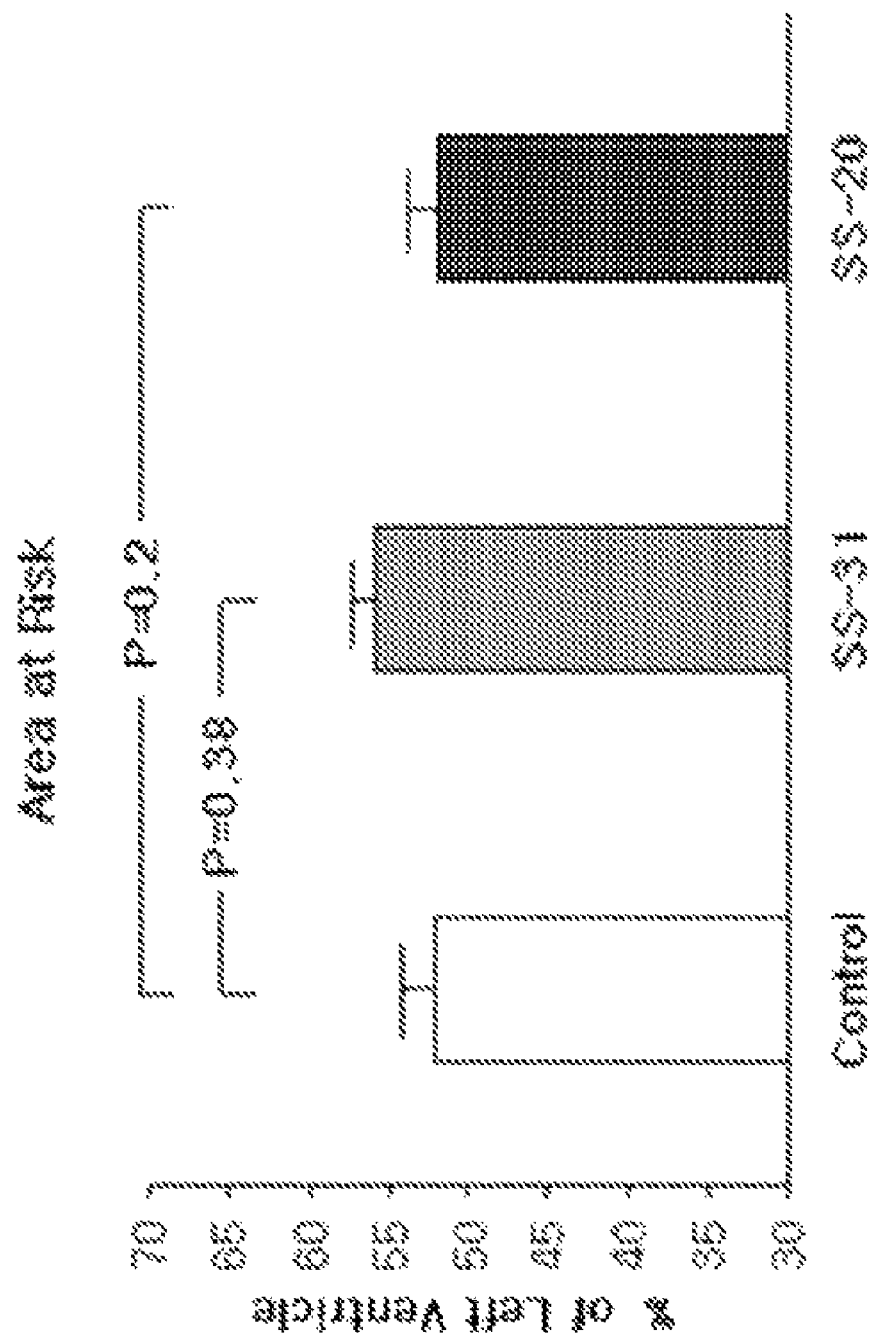
FIG. 9. The area at risk relative to the left ventricle after 1 hour ischemia followed by 1 hour of reperfusion in rats treated with control, SS-31 or SS-20 administered 30 min before ligation and 5 min before reperfusion. Bars represent group mean, brackets indicated S.E.M.
Figure 10:
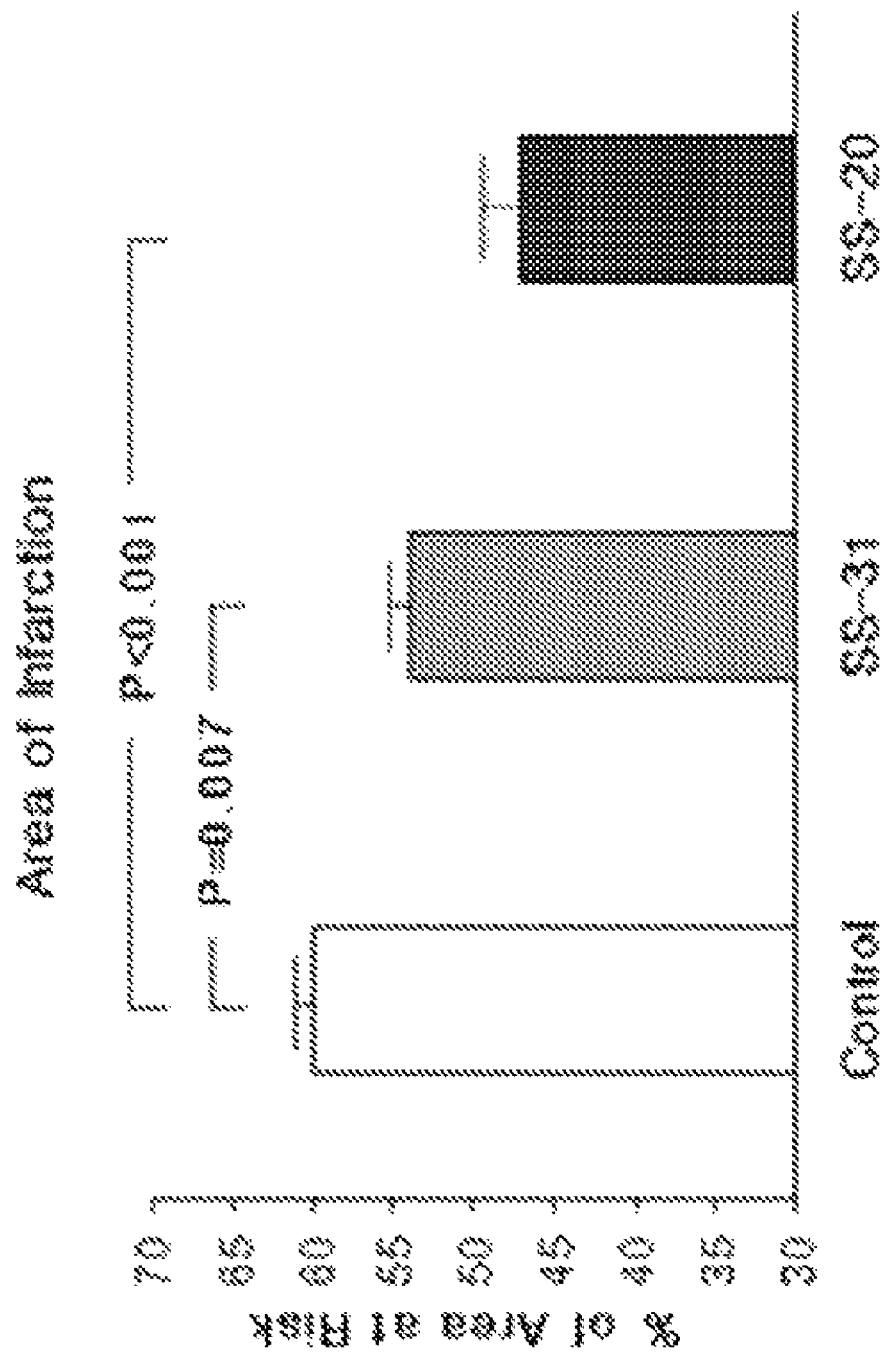
FIG. 10. Infarct size relative to the left ventricle after 1 hour ischemia followed by 1 hour of reperfusion in rats treated with control, SS-31 or SS-20 administered 30 min before ligation and 5 min before reperfusion. Bars represent group mean, brackets indicate S.E.M.

The chest was opened by left thoracotomy at the fourth intercostal space to expose the heart. The pericardium was removed, and the left atrial appendage was gently moved to reveal the location of the left coronary artery. The vein descending along the septum of the heart was used as the marker for the left coronary artery. A suture ligature (7.0 Prolene) along with a snare occluder was placed around the vein and left coronary artery close to the place of origin. The left anterior descending coronary artery was occluded by applying tension to the sling through a polyethylene 10 tubing and clamping. Successful occlusion was confirmed by elevation of the ST segment or the presence of deep S wave on the ECG and by cyanosis of the anterior wall of the left ventricle. Sixty minutes after occlusion, the snare occluder was released and reperfusion of the myocardium was visually confirmed. The heart was then reperfused for sixty minutes. The heart was arrested in diastole with an overdose of KCl and rapidly excised at the end of the experiment. The sham-operated control group was subjected to thoracotomy and passage of a silk ligature around the left coronary artery without ligation.
Determination of Area at Risk and Area of Infarction At the end of reperfusion, the left coronary artery was briefly re-occluded and Evans blue dye solution (2 ml of 2%, Sigma) was slowly injected into the jugular vein to distinguish the perfused area (blue staining) from the area at risk (no staining). The excised hearts were cut parallel to the atrioventricular groove into 5 slices (~1 mm thick) from base to apex. After removing all atrial and right ventricle tissues, all slices were scanned. The slices were incubated in a 2% solution of triphenyl-tetrazolium chloride (TTC, Sigma) in phosphate buffer for 20 min at 37° C. and pH of 7.4, and then immersed in 10% buffered formaldehyde for 14 days to distinguish the infarct area (unstained) from the viable myocardium (brick red staining). A prolonged formalin fixation was used to make infarct border zones easier to visualize. After a 14-day formalin immersion, the slices were scanned again and all scanned areas were quantified with NIH Imagesoftware. Area at risk (AAR) was expressed as a percentage of the left ventricle (LV). Area of infarction (AI) was calculated as a percentage of the AAR.
Assessment of Arrhythmias An ECG was recorded continuously from a standard lead II (AC AMP 700) inserted into the limbs of all rats. The ECG was printed at 25 mm/second. The cardiac arrhythmias were monitored and assessed in accordance with the Lambeth Convention. The assessment was performed in a blinded manner using the original paper recordings. A validated score was used to quantify the severity of cardiac arrhythmias. The score consisted of six types: 0, no ventricular extrasystoles (VES), ventricular tachycardia (VT) or ventricular fibrillation (VF); 1=VES; 2=one to five episodes of VT (more than four coupled VES); 3=more than five episodes of VT and/or one VF; 4=two to five episodes of VF; 5=more than five episodes of VF.
Statistical Analysis All values are expressed as mean±standard error of mean (S.E.M.). Statistical analyses were performed using SPSS version 10. Differences among groups in body weight, heart rate, arrhythmia, area at risk as a percentage of the left ventricle, and area of infarction as a percentage of the area at risk were analyzed using ANOVA. If significant differences were detected, comparisons between the control group and the 2 treatment groups were conducted using the Mann-Whitney U-test. A two-tailed p<0.05 was regarded as significant.
Results
Risk Areas and Infarct Sizes Representative slices of left ventricle form control, SS-31 and SS-20 groups are shown in FIG. 8. The AAR/LV ratio was similar among the three groups (52.1±2.5% in the control group, 55.9±1.4%, p=0.38 in the SS-31 group, and 52±2.1%, p=0.2 in the SS-20 group; FIG. 9). However, the AI/AAR ratio (FIG. 10) was significantly smaller in the SS-31 group (53.9±1.1%, p<0.01), in the SS-20 group (47.1±1.4%, p<0.01) than in the control group (59.9±1). Meanwhile, AAR/LV ratio of sham group was 50.3±4.6% (p=0.78 vs control) and AI/AAR ratio of sham group was 3.7±3.7% (p<0.05 vs control).

Heart Rate and Cardiac Arrhythmias

Compared with controls, there were no significant differences in body weight and heart rate in any of the two groups during the study period (Table 3). Almost all arrhythmias occurred between 2 and 15 min after coronary occlusion. These rats with arrhythmias showed isolated ventricular extrasystole or nonsustained ventricular tachycardia (VT), but not ventricular fibrillation. They were transient and recovered without therapy. Severity and occurrence rate of cardiac arrhythmias in SS-31 group (5 points, p<0.05) and SS-20 group (3 points, p<0.005) showed a significant reduction compared with control (13 points) during the entire study period.

TABLE 3

Body weight of all rats and heart rate during the course of the experiment.

| | Body weight | Heart Rate | | | | | |
|---|---|---|---|---|---|---|---|
| | | Baseline | Open chest | Ischemia | Ischemia | Reperfusion | Reperfusion |
| Control (n = 8) | 351 ± 18 | 246 ± 4 | 212 ± 9 | 186 ± 10 | 166 ± 8 | 176 ± 16 | 161 ± 4 |
| SS-31 (n = 8) | 340 ± 12 | 257 ± 10 | 236 ± 8 | 184 ± 14 | 169 ± 15 | 161 ± 12 | 164 ± 13 |
| SS-20 (n + 8) | 349 ± 18 | 255 ± 5 | 211 ± 10 | 191 ± 17 | 184 ± 15 | 182 ± 16 | 183 ± 12 |

All values are expressed as means ± S.E.M. There was no difference among study groups (P < 0.05).

What is claimed is:

1. A method for treating or preventing cytosolic $Ca^{2+}$ overload caused by hypoglycemia in a mammal in need thereof, the method comprising administering to the mammal an effective amount of an aromatic-cationic peptide having the amino acid sequence Lys-D-Arg-Tyr-$NH_2$, Phe-D-Arg-His, D-Tyr-Trp-Lys-$NH_2$, Trp-D-Lys-Tyr-Arg-$NH_2$, Tyr-His-D-Gly-Met, Phe-Arg-D-His-Asp, Tyr-D-Arg-Phe-Lys-Glu-$NH_2$, Met-Tyr-D-Lys-Phe-Arg, D-His-Glu-Lys-Tyr-D-Phe-Arg, Lys-D-Gln-Tyr-Arg-D-Phe-Trp-$NH_2$, Phe-D-Arg-Lys-Trp-Tyr-D-Arg-His, Gly-D-Phe-Lys-Tyr-His-D-Arg-Tyr-$NH_2$, Val-D-Lys-His-Tyr-D-Phe-Ser-Tyr-Arg-$NH_2$, Trp-Lys-Phe-D-Asp-Arg-Tyr-D-His-Lys, Lys-Trp-D-Tyr-Arg-Asn-Phe-Tyr-D-His-$NH_2$, Thr-Gly-Tyr-Arg-D-His-Phe-Trp-D-His-Lys, Asp-D-Trp-Lys-Tyr-D-His-Phe-Arg-D-Gly-Lys-$NH_2$, D-His-Lys-Tyr-D-Phe-Glu-D-Asp-D-His-D-Lys-Arg-Trp-$NH_2$, Ala-D-Phe-D-Arg-Tyr-Lys-D-Trp-His-D-Tyr-Gly-Phe, Tyr-D-His-Phe-D-Arg-Asp-Lys-D-Arg-His-Trp-D-His-Phe, Phe-Phe-D-Tyr-Arg-Glu-Asp-D-Lys-Arg-D-Arg-His-Phe-$NH_2$, Phe-Try-Lys-D-Arg-Trp-His-D-Lys-D-Lys-Glu-Arg-D-Tyr-Thr, Tyr-Asp-D-Lys-Tyr-Phe-D-Lys-D-Arg-Phe-Pro-D-Tyr-His-Lys Glu-Arg-D-Lys-Tyr-D-Val-Phe-D-His-Trp-Arg-D-Gly-Tyr-Arg-D-Met-$NH_2$, Arg-D-Leu-D-Tyr-Phe-Lys-Glu-D-Lys-Arg-D-Trp-Lys-D-Phe-Tyr-D-Arg-Gly, D-Glu-Asp-Lys-D-Arg-D-His-Phe-Phe-D-V al-Tyr-Arg-Tyr-D-Tyr-Arg-His-Phe-$NH_2$, Asp-Arg-D-Phe-Cys-Phe-D-Arg-D-Lys-Tyr-Arg-D-Tyr-Trp-D-His-Tyr-D-Phe-Lys-Phe, His-Tyr-D-Arg-Trp-Lys-Phe-D-Asp-Ala-Arg-Cys-D-Tyr-His-Phe-D-Lys-Tyr-His-Ser-$NH_2$, Gly-Ala-Lys-Phe-D-Lys-Glu-Arg-Tyr-His-D-Arg-D-Arg-Asp-Tyr-Trp-D-His-Trp-His-D-Lys-Asp, Thr-Tyr-Arg-D-Lys-Trp-Tyr-Glu-Asp-D-Lys-D-Arg-His-Phe-D-Tyr-Gly-Val-Ile-D-His-Arg-Tyr-Lys-$NH_2$, Tyr-D-Arg-Phe-Lys-$NH_2$, Tyr-D-Arg-Phe-Orn-$NH_2$, Tyr-D-Arg-Phe-Dab-$NH_2$, Tyr-D-Arg-Phe-Dap-$NH_2$, 2'6'Dmt-D-Arg-Phe-Lys-$NH_2$, 2'6'Dmt-D-Arg-Phe-Lys-Cys-NH$_2$, 2'6'Dmt-D-Arg-Phe-Lys-NH(CH$_2$)$_2$-NH-dns-NH$_2$, 2'6'Dmt-D-Arg-Phe-Lys-NH(CH$_2$)$_2$-NH-atn-NH$_2$, 2'6'Dmt-D-Arg-Phe-dnsLys-NH$_2$, 2'6'Dmt-D-Cit-Phe-Lys-NH$_2$, 2'6'Dmt-D-Cit-Phe-Ahp-NH$_2$, 2'6'Dmt-D-Arg-Phe-Orn-NH$_2$ 2'6'Dmt-D-Arg-Phe-Dab-NH$_2$, 2'6'Dmt-D-Arg-Phe-Dap-NH$_2$, 2'6'Dmt-D-Arg-Phe-Ahp(2-aminoheptanoic acid)-NH$_2$, Bio-2'6'Dmt-D-Arg-Phe-Lys-NH$_2$, 3'5'Dmt-D-Arg-Phe-Lys-NH$_2$, 3'5'Dmt-D-Arg-Phe-Orn-NH$_2$, 3'5'Dmt-D-Arg-Phe-Dab-NH$_2$, 3'5'Dmt-D-Arg-Phe-Dap-NH$_2$, Tyr-D-Arg-Tyr-Lys-NH$_2$, Tyr-D-Arg-Tyr-Orn-NH$_2$, Tyr-D-Arg-Tyr-Dab-NH$_2$, Tyr-D-Arg-Tyr-Dap-NH$_2$, 2'6'Dmt-D-Arg-Tyr-Lys-NH$_2$, 2'6'Dmt-D-Arg-Tyr-Orn-NH$_2$, 2'6'Dmt-D-Arg-Tyr-Dab-NH$_2$, 2'6'Dmt-D-Arg-Tyr-Dap-NH$_2$, 2'6'Dmt-D-Arg-2'6'Dmt-Lys-NH$_2$, 2'6'Dmt-D-Arg-2'6'Dmt-Orn-NH$_2$, 2'6'Dmt-D-Arg-2'6'Dmt-Dab-NH$_2$, 2'6'Dmt-D-Arg-2'6'Dmt-Dap-NH$_2$, 3'5Dmt-D-Arg-3'5Dmt-Arg-NH$_2$, 3'5Dmt-D-Arg-3'5Dmt-Lys-NH$_2$, 3'5Dmt-D-Arg-3'5Dmt-Orn-NH$_2$, 3'5Dmt-D-Arg-3'5Dmt-Dab-NH$_2$, Tyr-D-Lys-Phe-Dap-NH$_2$, Tyr-D-Lys-Phe-Arg-NH$_2$, Tyr-D-Lys-Phe-Lys-NH$_2$, Tyr-D-Lys-Phe-Orn-NH$_2$, 2'6'Dmt-D-Lys-Phe-Dab-NH$_2$ 2'6'Dmt-D-Lys-Phe-Dap-NH$_2$, 2'6'Dmt-D-Lys-Phe-Arg-NH$_2$, 2'6'Dmt-D-Lys-Phe-Lys-NH$_2$, 3'5'Dmt-D-Lys-Phe-Orn-NH$_2$, 3'5'Dmt-D-Lys-Phe-Dab-NH$_2$, 3'5'Dmt-D-Lys-Phe-Dap-NH$_2$, 3'5'Dmt-D-Lys-Phe-Arg-NH$_2$, Tyr-D-Lys-Tyr-Lys-NH$_2$, Tyr-D-Lys-Tyr-Orn-NH$_2$, Tyr-D-Lys-Tyr-Dab-NH$_2$, Tyr-D-Lys-Tyr-Dap-NH$_2$, 2'6'Dmt-D-Lys-Tyr-Lys-NH$_2$, 2'6'Dmt-D-Lys-Tyr-Orn-NH$_2$, 2'6'Dmt-D-Lys-Tyr-Dab-NH$_2$, 2'6'Dmt-D-Lys-Tyr-Dap-NH$_2$, 2'6'Dmt-D-Lys-2'6'Dmt-Lys-NH$_2$, 2'6'Dmt-D-Lys-2'6'Dmt-Orn-NH$_2$, 2 6'Dmt-D-Lys-2'6'Dmt-Dab-NH$_2$, 2'6'Dmt-D-Lys-2'6'Dmt-Dap-NH$_2$, 2'6'Dmt-D-Arg-Phe-dnsDap-NH$_2$, 2'6'Dmt-D-Arg-Phe-atnDap-NH$_2$, 3'5'Dmt-D-Lys-3'5'Dmt-Lys-NH$_2$, 3'5'Dmt-D-Lys-3'5'Dmt-Orn-NH$_2$, 3'5'Dmt-D-Lys-3'5'Dmt-Dab-NH$_2$, 3'5'Dmt-D-Lys-3'5'Dmt-Dap-NH$_2$, Tyr-D-Lys-Phe-Arg-NH$_2$, Tyr-D-Orn-Phe-Arg-NH$_2$, Tyr-D-Dab-Phe-Arg-NH$_2$, Tyr-D-Dap-Phe-Arg-NH$_2$, 2'6'Dmt-D-Arg-Phe-Arg-NH$_2$, 2'6'Dmt-D-Lys-Phe-Arg-NH$_2$, 2'6'Dmt-D-Orn-Phe-Arg-NH$_2$, 2'6'Dmt-D-Dab-Phe-Arg-NH$_2$, 3'5'Dmt-D-Dap-Phe-Arg-NH$_2$, 3'5'Dmt-D-Arg-Phe-Arg-NH$_2$, 3'5'Dmt-D-Lys-Phe-Arg-NH$_2$, 3'5'Dmt-D-Orn-Phe-Arg-NH$_2$, Tyr-D-Lys-Tyr-Arg-NH$_2$, Tyr-D-Orn-Tyr-Arg-NH$_2$, Tyr-D-Dab-Tyr-Arg-NH$_2$, Tyr-D-Dap-Tyr-Arg-NH$_2$, 2'6'Dmt-D-Arg-2'6'Dmt-Arg-NH$_2$, 2'6'Dmt-D-Lys-2'6'Dmt-Arg-NH$_2$, 2'6'Dmt-D-Orn-2'6'Dmt-Arg-NH$_2$, 2'6'Dmt-D-Dab-2'6'Dmt-Arg-NH$_2$, 3'5'Dmt-D-Dap-3'5'Dmt-Arg-NH$_2$, 3'5'Dmt-D-Arg-3'5'Dmt-Arg-NH$_2$, 3'5'Dmt-D-Lys-3'5'Dmt-Arg-NH$_2$, 3'5'Dmt-D-Orn-3'5'Dmt-Arg-NH$_2$, Mmt-D-Arg-Phe-Lys-NH$_2$, Mmt-D-Arg-Phe-Orn-NH$_2$, Mmt-D-Arg-Phe-Dab-NH$_2$, Mmt-D-Arg-Phe-Dap-NH$_2$, Tmt-D-Arg-Phe-Lys-NH$_2$, Tmt-D-Arg-Phe-Orn-NH$_2$, Tmt-D-Arg-Phe-Dab-NH$_2$, Tmt-D-Arg-Phe-Dap-NH$_2$, Hmt-D-Arg-Phe-Lys-NH$_2$, Hmt-D-Arg-Phe-Orn-NH$_2$, Hmt-D-Arg-Phe-Dab-NH$_2$, Hmt-D-Arg-Phe-Dap-NH$_2$, Mmt-D-Lys-Phe-Lys-NH$_2$, Mmt-D-Lys-Phe-Orn-NH$_2$, Mmt-D-Lys-Phe-Dab-NH$_2$, Mmt-D-Lys-Phe-Dap-NH$_2$, Mmt-D-Lys-Phe-Arg-NH$_2$, Tmt-D-Lys-Phe-Lys-NH$_2$, Tmt-D-Lys-Phe-Orn-NH$_2$, Tmt-D-Lys-Phe-Dab-NH$_2$, Tmt-D-Lys-Phe-Dap-NH$_2$, Tmt-D-Lys-Phe-Arg-NH$_2$, Hmt-D-Lys-Phe-Lys-NH$_2$, Hmt-D-Lys-Phe-Orn-NH$_2$, Hmt-D-Lys-Phe-Dab-NH$_2$, Hmt-D-Lys-Phe-Dap-NH$_2$, Hmt-D-Lys-Phe-Arg-NH$_2$, Mmt-D-Lys-Phe-Arg-NH$_2$, Mmt-D-Orn-Phe-Arg-NH$_2$, Mmt-D-Dab-Phe-Arg-NH$_2$, Mmt-D-Dap-Phe-Arg-NH$_2$, Mmt-D-Arg-Phe-Arg-NH$_2$, Tmt-D-Lys-Phe-Arg-NH$_2$, Tmt-D-Orn-Phe-Arg-NH$_2$, Tmt-D-Dab-Phe-Arg-NH$_2$, Tmt-D-Dap-Phe-Arg-NH$_2$, Tmt-D-Arg-Phe-Arg-NH$_2$, Hmt-D-Lys-Phe-Arg-NH$_2$ Hmt-D-Orn-Phe-Arg-NH$_2$, Hmt-D-Dab-Phe-Arg-NH$_2$, Hmt-D-Dap-Phe-Arg-NH$_2$, Hmt-D-Arg-Phe-Arg-NH$_2$, D-Arg-2'6'Dmt-Lys-Phe-NH$_2$, D-Arg-2'6'Dmt-Phe-Lys-NH$_2$, D-Arg-Phe-Lys-2'6'Dmt-NH$_2$, D-Arg-Phe-2'6'Dmt-Lys-NH$_2$, D-Arg-Lys-2'6'Dmt-Phe-NH$_2$, D-Arg-Lys-Phe-2'6'Dmt-NH$_2$, Phe-Lys-2'6'Dmt-D-Arg-NH$_2$, Phe-Lys-D-Arg-2'6'Dmt-NH$_2$, Phe-D-Arg-2'6'Dmt-Lys-NH$_2$, Phe-D-Arg-Lys-2'6'Dmt-NH$_2$, Phe-2'6'Dmt-D-Arg-Lys-NH$_2$, Phe-2'6'Dmt-Lys-D-Arg-NH$_2$, Lys-Phe-D-Arg-2'6'Dmt-NH$_2$, Lys-Phe-2'6'Dmt-D-Arg-NH$_2$, Lys-2'6'Dmt-D-Arg-Phe-NH$_2$, Lys-2'6'Dmt-Phe-D-Arg-NH$_2$, Lys-D-Arg-Phe-2'6'Dmt-NH$_2$, Lys-D-Arg-2'6'Dmt-Phe-NH$_2$, D-Arg-2'6'Dmt-D-Arg-Phe-NH$_2$, D-Arg-2'6'Dmt-D-Arg-2'6'Dmt-NH$_2$, D-Arg-2'6'Dmt-D-Arg-Tyr-NH$_2$, D-Arg-2'6'Dmt-D-Arg-Trp-NH$_2$, Trp-D-Arg-Phe-Lys-NH$_2$, Trp-D-Arg-Tyr-Lys-NH$_2$, Trp-D-Arg-Trp-Lys-NH$_2$, Trp-D-Arg-2'6'Dmt-Lys-NH$_2$ D-Arg-Trp-Lys-Phe-NH$_2$, D-Arg-Trp-Phe-Lys-NH$_2$, D-Arg-Trp-Lys-2'6'Dmt-NH$_2$ D-Arg-Trp-2'6'Dmt-Lys-NH$_2$, D-Arg-Lys-Trp-Phe-NH$_2$, D-Arg-Lys-Trp-2'6'Dmt-NH$_2$, Cha-D-Arg-Phe-Lys-NH$_2$,
or Ala-D-Arg-Phe-Lys-NH$_2$.

2. The method of claim 1, wherein the mammal is a human.

3. The method of claim 1, wherein the peptide is administered orally, topically, intranasally, systemically, intravenously, subcutaneously, intramuscularly, intrathecally, or transdermally.

4. The method of claim 1, wherein the peptide is combined with a pharmaceutically acceptable carrier prior to administration to the mammal.

5. The method of claim 1, wherein the peptide has the amino acid sequence D-Arg-2'6'Dmt-Lys-Phe-NH$_2$.

6. The method of claim 1, wherein the peptide has the amino acid sequence 2'6'Dmt-D-Arg-Phe-Lys-NH$_2$.

7. The method of claim 1, wherein the peptide has the amino acid sequence Phe-D-Arg-Phe-Lys-NH$_2$.

8. A method for preventing Ca$^{2+}$-induced necrotic cell death caused by hypoglycemia in a mammal in need thereof, the method comprising administering to the mammal an effective amount of an aromatic-cationic peptide having the amino acid sequence

```
Lys-D-Arg-Tyr-NH2,

Phe-D-Arg-His,

D-Tyr-Trp-Lys-NH2,

Trp-D-Lys-Tyr-Arg-NH2,

Tyr-His-D-Gly-Met,

Phe-Arg-D-His-Asp,

Tyr-D-Arg-Phe-Lys-Glu-NH2,

Met-Tyr-D-Lys-Phe-Arg,

D-His-Glu-Lys-Tyr-D-Phe-Arg,

Lys-D-Gln-Tyr-Arg-D-Phe-Trp-NH2,

Phe-D-Arg-Lys-Trp-Tyr-D-Arg-His,

Gly-D-Phe-Lys-Tyr-His-D-Arg-Tyr-NH2,

Val-D-Lys-His-Tyr-D-Phe-Ser-Tyr-Arg-NH2,

Trp-Lys-Phe-D-Asp-Arg-Tyr-D-His-Lys,

Lys-Trp-D-Tyr-Arg-Asn-Phe-Tyr-D-His-NH2,

Thr-Gly-Tyr-Arg-D-His-Phe-Trp-D-His-Lys,

Asp-D-Trp-Lys-Tyr-D-His-Phe-Arg-D-Gly-Lys-NH2,

D-His-Lys-Tyr-D-Phe-Glu-D-Asp-D-His-D-Lys-Arg-Trp-
NH2,

Ala-D-Phe-D-Arg-Tyr-Lys-D-Trp-His-D-Tyr-Gly-Phe,

Tyr-D-His-Phe-D-Arg-Asp-Lys-D-Arg-His-Trp-D-His-
Phe,

Phe-Phe-D-Tyr-Arg-Glu-Asp-D-Lys-Arg-D-Arg-His-Phe-
NH2,

Phe-Try-Lys-D-Arg-Trp-His-D-Lys-D-Lys-Glu-Arg-D-
Tyr-Thr,

Tyr-Asp-D-Lys-Tyr-Phe-D-Lys-D-Arg-Phe-Pro-D-Tyr-
His-Lys Glu-Arg-D-Lys-Tyr-D-Val-Phe-D-His-Trp-Arg-
D-Gly-Tyr-Arg-D-Met-NH2,

Arg-D-Leu-D-Tyr-Phe-Lys-Glu-D-Lys-Arg-D-Trp-Lys-D-
Phe-Tyr-D-Arg-Gly,

D-Glu-Asp-Lys-D-Arg-D-His-Phe-Phe-D-Val-Tyr-Arg-
Tyr-D-Tyr-Arg-His-Phe-NH2,

Asp-Arg-D-Phe-Cys-Phe-D-Arg-D-Lys-Tyr-Arg-D-Tyr-
Trp-D-His-Tyr-D-Phe-Lys-Phe,

His-Tyr-D-Arg-Trp-Lys-Phe-D-Asp-Ala-Arg-Cys-D-Tyr-
His-Phe-D-Lys-Tyr-His-Ser-NH2,

Gly-Ala-Lys-Phe-D-Lys-Glu-Arg-Tyr-His-D-Arg-D-Arg-
Asp-Tyr-Trp-D-His-Trp-His-D-Lys-Asp,

Thr-Tyr-Arg-D-Lys-Trp-Tyr-Glu-Asp-D-Lys-D-Arg-His-
Phe-D-Tyr-Gly-Val-Ile-D-His-Arg-Tyr-Lys-NH2,

Tyr-D-Arg-Phe-Lys-NH2,

Tyr-D-Arg-Phe-Orn-NH2,

Tyr-D-Arg-Phe-Dab-NH2,

Tyr-D-Arg-Phe-Dap-NH2,

2'6'Dmt-D-Arg-Phe-Lys-NH2,

2'6'Dmt-D-Arg-Phe-Lys-Cys-NH2,

2'6'Dmt-D-Arg-Phe-Lys-NH(CH2)2-NH-dns-NH2,

2'6'Dmt-D-Arg-Phe-Lys-NH(CH2)2-NH-atn-NH2,

2'6'Dmt-D-Arg-Phe-dnsLys-NH2,

2'6'Dmt-D-Cit-Phe-Lys-NH2,

2'6'Dmt-D-Cit-Phe-Ahp-NH2,

2'6'Dmt-D-Arg-Phe-Orn-NH2

2'6'Dmt-D-Arg-Phe-Dab-NH2,

2'6'Dmt-D-Arg-Phe-Dap-NH2,

2'6'Dmt-D-Arg-Phe-Ahp(2-aminoheptanoic acid)-NH2,

Bio-2'6'Dmt-D-Arg-Phe-Lys-NH2,

3'5'Dmt-D-Arg-Phe-Lys-NH2,

3'5'Dmt-D-Arg-Phe-Orn-NH2,

3'5'Dmt-D-Arg-Phe-Dab-NH2,

3'5'Dmt-D-Arg-Phe-Dap-NH2,

Tyr-D-Arg-Tyr-Lys-NH2,

Tyr-D-Arg-Tyr-Orn-NH2,

Tyr-D-Arg-Tyr-Dab-NH2,

Tyr-D-Arg-Tyr-Dap-NH2,

2'6'Dmt-D-Arg-Tyr-Lys-NH2,

2'6'Dmt-D-Arg-Tyr-Orn-NH2,
```

-continued

2'6'Dmt-D-Arg-Tyr-Dab-NH$_2$,

2'6'Dmt-D-Arg-Tyr-Dap-NH$_2$,

2'6'Dmt-D-Arg-2'6'Dmt-Lys-NH$_2$,

2'6'Dmt-D-Arg-2'6'Dmt-Orn-NH$_2$,

2'6'Dmt-D-Arg-2'6'Dmt-Dab-NH$_2$,

2'6'Dmt-D-Arg-2'6'Dmt-Dap-NH$_2$,

3'5Dmt-D-Arg-3'5Dmt-Arg-NH$_2$,

3'5Dmt-D-Arg-3'5Dmt-Lys-NH$_2$,

3'5Dmt-D-Arg-3'5Dmt-Orn-NH$_2$,

3'5Dmt-D-Arg-3'5Dmt-Dab-NH$_2$,

Tyr-D-Lys-Phe-Dap-NH$_2$,

Tyr-D-Lys-Phe-Arg-NH$_2$,

Tyr-D-Lys-Phe-Lys-NH$_2$,

Tyr-D-Lys-Phe-Orn-NH$_2$,

2'6'Dmt-D-Lys-Phe-Dab-NH$_2$

2'6'Dmt-D-Lys-Phe-Dap-NH$_2$,

2'6'Dmt-D-Lys-Phe-Arg-NH$_2$,

2'6'Dmt-D-Lys-Phe-Lys-NH$_2$,

3'5'Dmt-D-Lys-Phe-Orn-NH$_2$,

3'5'Dmt-D-Lys-Phe-Dab-NH$_2$,

3'5'Dmt-D-Lys-Phe-Dap-NH$_2$,

3'5'Dmt-D-Lys-Phe-Arg-NH$_2$,

Tyr-D-Lys-Tyr-Lys-NH$_2$,

Tyr-D-Lys-Tyr-Orn-NH$_2$,

Tyr-D-Lys-Tyr-Dab-NH$_2$,

Tyr-D-Lys-Tyr-Dap-NH$_2$,

2'6'Dmt-D-Lys-Tyr-Lys-NH$_2$,

2'6'Dmt-D-Lys-Tyr-Orn-NH$_2$,

2'6'Dmt-D-Lys-Tyr-Dab-NH$_2$,

2'6'Dmt-D-Lys-Tyr-Dap-NH$_2$,

2'6'Dmt-D-Lys-2'6'Dmt-Lys-NH$_2$,

2'6'Dmt-D-Lys-2'6'Dmt-Orn-NH$_2$,

2'6'Dmt-D-Lys-2'6'Dmt-Dab-NH$_2$,

2'6'Dmt-D-Lys-2'6'Dmt-Dap-NH$_2$,

2'6'Dmt-D-Arg-Phe-dnsDap-NH$_2$,

2'6'Dmt-D-Arg-Phe-atnDap-NH$_2$,

3'5'Dmt-D-Lys-3'5'Dmt-Lys-NH$_2$,

3'5'Dmt-D-Lys-3'5'Dmt-Orn-NH$_2$,

3'5'Dmt-D-Lys-3'5'Dmt-Dab-NH$_2$,

3'5'Dmt-D-Lys-3'5'Dmt-Dap-NH$_2$,

Tyr-D-Lys-Phe-Arg-NH$_2$,

-continued

Tyr-D-Orn-Phe-Arg-NH$_2$,

Tyr-D-Dab-Phe-Arg-NH$_2$,

Tyr-D-Dap-Phe-Arg-NH$_2$,

2'6'Dmt-D-Arg-Phe-Arg-NH$_2$,

2'6'Dmt-D-Lys-Phe-Arg-NH$_2$,

2'6'Dmt-D-Orn-Phe-Arg-NH$_2$,

2'6'Dmt-D-Dab-Phe-Arg-NH$_2$,

3'5'Dmt-D-Dap-Phe-Arg-NH$_2$,

3'5'Dmt-D-Arg-Phe-Arg-NH$_2$,

3'5'Dmt-D-Lys-Phe-Arg-NH$_2$,

3'5'Dmt-D-Orn-Phe-Arg-NH$_2$,

Tyr-D-Lys-Tyr-Arg-NH$_2$,

Tyr-D-Orn-Tyr-Arg-NH$_2$,

Tyr-D-Dab-Tyr-Arg-NH$_2$,

Tyr-D-Dap-Tyr-Arg-NH$_2$,

2'6'Dmt-D-Arg-2'6'Dmt-Arg-NH$_2$,

2'6'Dmt-D-Lys-2'6'Dmt-Arg-NH$_2$,

2'6'Dmt-D-Orn-2'6'Dmt-Arg-NH$_2$,

2'6'Dmt-D-Dab-2'6'Dmt-Arg-NH$_2$,

3'5'Dmt-D-Dap-3'5'Dmt-Arg-NH$_2$,

3'5'Dmt-D-Arg-3'5'Dmt-Arg-NH$_2$,

3'5'Dmt-D-Lys-3'5'Dmt-Arg-NH$_2$,

3'5'Dmt-D-Orn-3'5'Dmt-Arg-NH$_2$,

Mmt-D-Arg-Phe-Lys-NH$_2$,

Mmt-D-Arg-Phe-Orn-NH$_2$,

Mmt-D-Arg-Phe-Dab-NH$_2$,

Mmt-D-Arg-Phe-Dap-NH$_2$,

Tmt-D-Arg-Phe-Lys-NH$_2$,

Tmt-D-Arg-Phe-Orn-NH$_2$,

Tmt-D-Arg-Phe-Dab-NH$_2$,

Tmt-D-Arg-Phe-Dap-NH$_2$,

Hmt-D-Arg-Phe-Lys-NH$_2$,

Hmt-D-Arg-Phe-Orn-NH$_2$,

Hmt-D-Arg-Phe-Dab-NH$_2$,

Hmt-D-Arg-Phe-Dap-NH$_2$,

Mmt-D-Lys-Phe-Lys-NH$_2$,

Mmt-D-Lys-Phe-Orn-NH$_2$,

Mmt-D-Lys-Phe-Dab-NH$_2$,

Mmt-D-Lys-Phe-Dap-NH$_2$,

Mmt-D-Lys-Phe-Arg-NH$_2$,

Tmt-D-Lys-Phe-Lys-NH$_2$,

Tmt-D-Lys-Phe-Orn-NH$_2$,

Tmt-D-Lys-Phe-Dab-NH$_2$,

Tmt-D-Lys-Phe-Dap-NH$_2$,

Tmt-D-Lys-Phe-Arg-NH$_2$,

Hmt-D-Lys-Phe-Lys-NH$_2$,

Hmt-D-Lys-Phe-Orn-NH$_2$,

Hmt-D-Lys-Phe-Dab-NH$_2$,

Hmt-D-Lys-Phe-Dap-NH$_2$,

Hmt-D-Lys-Phe-Arg-NH$_2$,

Mmt-D-Lys-Phe-Arg-NH$_2$,

Mmt-D-Orn-Phe-Arg-NH$_2$,

Mmt-D-Dab-Phe-Arg-NH$_2$,

Mmt-D-Dap-Phe-Arg-NH$_2$,

Mmt-D-Arg-Phe-Arg-NH$_2$,

Tmt-D-Lys-Phe-Arg-NH$_2$,

Tmt-D-Orn-Phe-Arg-NH$_2$,

Tmt-D-Dab-Phe-Arg-NH$_2$,

Tmt-D-Dap-Phe-Arg-NH$_2$,

Tmt-D-Arg-Phe-Arg-NH$_2$,

Hmt-D-Lys-Phe-Arg-NH$_2$

Hmt-D-Orn-Phe-Arg-NH$_2$,

Hmt-D-Dab-Phe-Arg-NH$_2$,

Hmt-D-Dap-Phe-Arg-NH$_2$,

Hmt-D-Arg-Phe-Arg-NH$_2$,

D-Arg-2'6'Dmt-Lys-Phe-NH$_2$,

D-Arg-2'6'Dmt-Phe-Lys-NH$_2$,

D-Arg-Phe-Lys-2'6'Dmt-NH$_2$,

D-Arg-Phe-2'6'Dmt-Lys-NH$_2$,

D-Arg-Lys-2'6'Dmt-Phe-NH$_2$,

D-Arg-Lys-Phe-2'6'Dmt-NH$_2$,

Phe-Lys-2'6'Dmt-D-Arg-NH$_2$,

Phe-Lys-D-Arg-2'6'Dmt-NH$_2$,

Phe-D-Arg-2'6'Dmt-Lys-NH$_2$,

Phe-D-Arg-Lys-2'6'Dmt-NH$_2$,

Phe-2'6'Dmt-D-Arg-Lys-NH$_2$,

Phe-2'6'Dmt-Lys-D-Arg-NH$_2$,

Lys-Phe-D-Arg-2'6'Dmt-NH$_2$,

Lys-Phe-2'6'Dmt-D-Arg-NH$_2$,

Lys-2'6'Dmt-D-Arg-Phe-NH$_2$,

Lys-2'6'Dmt-Phe-D-Arg-NH$_2$,

Lys-D-Arg-Phe-2'6'Dmt-NH$_2$,

Lys-D-Arg-2'6'Dmt-Phe-NH$_2$,

D-Arg-2'6'Dmt-D-Arg-Phe-NH$_2$,

D-Arg-2'6'Dmt-D-Arg-2'6'Dmt-NH$_2$,

D-Arg-2'6'Dmt-D-Arg-Tyr-NH$_2$,

D-Arg-2'6'Dmt-D-Arg-Trp-NH$_2$,

Trp-D-Arg-Phe-Lys-NH$_2$,

Trp-D-Arg-Tyr-Lys-NH$_2$,

Trp-D-Arg-Trp-Lys-NH$_2$,

Trp-D-Arg-2'6'Dmt-Lys-NH$_2$

D-Arg-Trp-Lys-Phe-NH$_2$,

D-Arg-Trp-Phe-Lys-NH$_2$,

D-Arg-Trp-Lys-2'6'Dmt-NH$_2$

D-Arg-Trp-2'6'Dmt-Lys-NH$_2$,

D-Arg-Lys-Trp-Phe-NH$_2$,

D-Arg-Lys-Trp-2'6'Dmt-NH$_2$,

Cha-D-Arg-Phe-Lys-NH$_2$,
or

Ala-D-Arg-Phe-Lys-NH$_2$.

9. The method of claim 8, wherein the mammal is a human.

10. The method of claim 8, wherein the peptide is administered orally, topically, intranasally, systemically, intravenously, subcutaneously, intramuscularly, intrathecally, or transdermally.

11. The method of claim 8, wherein the peptide is combined with a pharmaceutically acceptable carrier prior to administration to the mammal.

12. The method of claim 8, wherein the peptide has the amino acid sequence D-Arg-2'6'Dmt-Lys-Phe-NH$_2$.

13. The method of claim 8, wherein the peptide has the amino acid sequence 2'6'Dmt-D-Arg-Phe-Lys-NH$_2$.

14. The method of claim 8, wherein the peptide has the amino acid sequence Phe-D-Arg-Phe-Lys-NH$_2$.

15. A method of regulating cytosolic Ca$^{2+}$ levels in hypoglycemia in a mammal in need thereof, the method comprising administering to the mammal an effective amount of an aromatic-cationic peptide having the amino acid sequence Lys-D-Arg-Tyr-NH$_2$, Phe-D-Arg-His, D-Tyr-Trp-Lys-NH$_2$, Trp-D-Lys-Tyr-Arg-NH$_2$, Tyr-His-D-Gly-Met, Phe-Arg-D-His-Asp, Tyr-D-Arg-Phe-Lys-Glu-NH$_2$, Met-Tyr-D-Lys-Phe-Arg, D-His-Glu-Lys-Tyr-D-Phe-Arg, Lys-D-Gln-Tyr-Arg-D-Phe-Trp-NH$_2$, Phe-D-Arg-Lys-Trp-Tyr-D-Arg-His, Gly-D-Phe-Lys-Tyr-His-D-Arg-Tyr-NH$_2$, Val-D-Lys-His-Tyr-D-Phe-Ser-Tyr-Arg-NH$_2$, Trp-Lys-Phe-D-Asp-Arg-Tyr-D-His-Lys, Lys-Trp-D-Tyr-Arg-Asn-Phe-Tyr-D-His-NH$_2$, Thr-Gly-Tyr-Arg-D-His-Phe-Trp-D-His-Lys, Asp-D-Trp-Lys-Tyr-D-His-Phe-Arg-D-Gly-Lys-NH$_2$, D-His-Lys-Tyr-D-Phe-Glu-D-Asp-D-His-D-Lys-Arg-Trp-NH$_2$, Ala-D-Phe-D-Arg-Tyr-Lys-D-Trp-His-D-Tyr-Gly-Phe, Tyr-D-His-Phe-D-Arg-Asp-Lys-D-Arg-His-Trp-D-His-Phe, Phe-Phe-D-Tyr-Arg-Glu-Asp-D-Lys-Arg-D-Arg-His-Phe-NH$_2$, Phe-Try-Lys-D-Arg-Trp-His-D-Lys-D-Lys-Glu-Arg-D-Tyr-Thr, Tyr-Asp-D-Lys-Tyr-Phe-D-Lys-D-Arg-Phe-Pro-D-Tyr-His-Lys Glu-Arg-D-Lys-Tyr-D-Val-Phe-D-His-Trp-Arg-D-Gly-Tyr-Arg-D-Met-NH$_2$, Arg-D-Leu-D-Tyr-Phe-Lys-Glu-D-Lys-Arg-D-Trp-Lys-D-Phe-Tyr-D-Arg-Gly, D-Glu-Asp-Lys-D-Arg-D-His-Phe-Phe-D-V al-Tyr-Arg-Tyr-D-Tyr-Arg-His-Phe-NH$_2$, Asp-Arg-D-Phe-Cys-Phe-D-Arg-D-Lys-Tyr-Arg-D-Tyr-Trp-D-His-Tyr-D-Phe-Lys-Phe, His-Tyr-D-Arg-Trp-Lys-Phe-D-Asp-Ala-Arg-Cys-D-Tyr-His-Phe-D-Lys-Tyr-His-Ser-NH$_2$, Gly-Ala-Lys-Phe-D-Lys-Glu-Arg-Tyr-His-D-Arg-D-Arg-Asp-Tyr-Trp-D-His-Trp-His-D-Lys-Asp, Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$, Tyr-D-Arg-Phe-Lys-NH$_2$, Tyr-D-Arg-Phe-Orn-NH$_2$, Tyr-D-Arg-Phe-Dab-NH$_2$, Tyr-D-Arg-Phe-Dap-NH$_2$, 2'6'Dmt-D-Arg-Phe-Lys-NH$_2$, 2'6'Dmt-D-Arg-Phe-Lys-Cys-NH$_2$, 2'6'Dmt-D-Arg-Phe-Lys-NH(CH$_2$)$_2$-NH-dns-NH$_2$, 2'6'Dmt-D-Arg-Phe-Lys-NH(CH$_2$)$_2$-NH-atn-NH$_2$, 2'6'Dmt-D-Arg-Phe-dnsLys-NH$_2$, 2'6'Dmt-D-Cit-Phe-Lys-NH$_2$, 2'6'Dmt-D-Cit-Phe-Ahp-NH$_2$, 2'6'Dmt-D-Arg-Phe-Orn-NH$_2$ 2'6'Dmt-D-Arg-Phe-Dab-NH$_2$, 2'6'Dmt-D-Arg-Phe-Dap-NH$_2$, 2'6'Dmt-D-Arg-Phe-Ahp(2-aminoheptanoic acid)-NH$_2$, Bio-2'6'Dmt-D-Arg-Phe-Lys-NH$_2$, 3'5'Dmt-D-Arg-Phe-Lys-NH$_2$, 3'5'Dmt-D-Arg-Phe-Orn-NH$_2$, 3'5'Dmt-D-Arg-Phe-Dab-NH$_2$, 3'5'Dmt-D-Arg-Phe-Dap-NH$_2$, Tyr-D-Arg-Tyr-Lys-NH$_2$, Tyr-D-Arg-Tyr-Orn-NH$_2$, Tyr-D-Arg-Tyr-Dab-NH$_2$, Tyr-D-Arg-Tyr-Dap-NH$_2$, 2'6'Dmt-D-Arg-Tyr-Lys-NH$_2$, 2'6'Dmt-D-Arg-Tyr-Orn-NH$_2$, 2'6'Dmt-D-Arg-Tyr-Dab-NH$_2$, 2'6'Dmt-D-Arg-Tyr-Dap-NH$_2$, 2'6'Dmt-D-Arg-2'6'Dmt-Lys-NH$_2$, 2'6'Dmt-D-Arg-2'6'Dmt-Orn-NH$_2$, 2'6'Dmt-D-Arg-2'6'Dmt-Dab-NH$_2$, 2'6'Dmt-D-Arg-2'6'Dmt-Dap-NH$_2$, 3'5Dmt-D-Arg-3'5Dmt-Arg-NH$_2$, 3'5Dmt-D-Arg-3'5Dmt-Lys-NH$_2$, 3'5Dmt-D-Arg-3'5Dmt-Orn-NH$_2$, 3'5Dmt-D-Arg-3'5Dmt-Dab-NH$_2$, Tyr-D-Lys-Phe-Dap-NH$_2$, Tyr-D-Lys-Phe-Arg-NH$_2$, Tyr-D-Lys-Phe-Lys-NH$_2$, Tyr-D-Lys-Phe-Orn-NH$_2$, 2'6'Dmt-D-Lys-Phe-Dab-NH$_2$ 2'6'Dmt-D-Lys-Phe-Dap-NH$_2$, 2'6'Dmt-D-Lys-Phe-Arg-NH$_2$, 2'6'Dmt-D-Lys-Phe-Lys-NH$_2$, 3'5'Dmt-D-Lys-Phe-Orn-NH$_2$, 3'5'Dmt-D-Lys-Phe-Dab-NH$_2$, 3'5'Dmt-D-Lys-Phe-Dap-NH$_2$, 3'5'Dmt-D-Lys-Phe-Arg-NH$_2$, Tyr-D-Lys-Tyr-Lys-NH$_2$, Tyr-D-Lys-Tyr-Orn-NH$_2$, Tyr-D-Lys-Tyr-Dab-NH$_2$, Tyr-D-Lys-Tyr-Dap-NH$_2$, -continued 2'6'Dmt-D-Lys-Tyr-Lys-NH$_2$, 2'6'Dmt-D-Lys-Tyr-Orn-NH$_2$, 2'6'Dmt-D-Lys-Tyr-Dab-NH$_2$, 2'6'Dmt-D-Lys-Tyr-Dap-NH$_2$, 2'6'Dmt-D-Lys-2'6'Dmt-Lys-NH$_2$, 2'6'Dmt-D-Lys-2'6'Dmt-Orn-NH$_2$, 2'6'Dmt-D-Lys-2'6'Dmt-Dab-NH$_2$, 2'6'Dmt-D-Lys-2'6'Dmt-Dap-NH$_2$, 2'6'Dmt-D-Arg-Phe-dnsDap-NH$_2$, 2'6'Dmt-D-Arg-Phe-atnDap-NH$_2$, 3'5'Dmt-D-Lys-3'5'Dmt-Lys-NH$_2$, 3'5'Dmt-D-Lys-3'5'Dmt-Orn-NH$_2$, 3'5'Dmt-D-Lys-3'5'Dmt-Dab-NH$_2$, 3'5'Dmt-D-Lys-3'5'Dmt-Dap-NH$_2$, Tyr-D-Lys-Phe-Arg-NH$_2$, Tyr-D-Orn-Phe-Arg-NH$_2$, Tyr-D-Dab-Phe-Arg-NH$_2$, Tyr-D-Dap-Phe-Arg-NH$_2$, 2'6'Dmt-D-Arg-Phe-Arg-NH$_2$, 2'6'Dmt-D-Lys-Phe-Arg-NH$_2$, 2'6'Dmt-D-Orn-Phe-Arg-NH$_2$, 2'6'Dmt-D-Dab-Phe-Arg-NH$_2$, 3'5'Dmt-D-Dap-Phe-Arg-NH$_2$, 3'5'Dmt-D-Arg-Phe-Arg-NH$_2$, 3'5'Dmt-D-Lys-Phe-Arg-NH$_2$, 3'5'Dmt-D-Orn-Phe-Arg-NH$_2$, Tyr-D-Lys-Tyr-Arg-NH$_2$, Tyr-D-Orn-Tyr-Arg-NH$_2$, Tyr-D-Dab-Tyr-Arg-NH$_2$, Tyr-D-Dap-Tyr-Arg-NH$_2$, 2'6'Dmt-D-Arg-2'6'Dmt-Arg-NH$_2$, 2'6'Dmt-D-Lys-2'6'Dmt-Arg-NH$_2$, 2'6'Dmt-D-Orn-2'6'Dmt-Arg-NH$_2$, 2'6'Dmt-D-Dab-2'6'Dmt-Arg-NH$_2$, 3'5'Dmt-D-Dap-3'5'Dmt-Arg-NH$_2$, 3'5'Dmt-D-Arg-3'5'Dmt-Arg-NH$_2$, 3'5'Dmt-D-Lys-3'5'Dmt-Arg-NH$_2$, 3'5'Dmt-D-Orn-3'5'Dmt-Arg-NH$_2$, Mmt-D-Arg-Phe-Lys-NH$_2$, Mmt-D-Arg-Phe-Orn-NH$_2$, Mmt-D-Arg-Phe-Dab-NH$_2$, -continued Mmt-D-Arg-Phe-Dap-NH$_2$, Tmt-D-Arg-Phe-Lys-NH$_2$, Tmt-D-Arg-Phe-Orn-NH$_2$, Tmt-D-Arg-Phe-Dab-NH$_2$, Tmt-D-Arg-Phe-Dap-NH$_2$, Hmt-D-Arg-Phe-Lys-NH$_2$, Hmt-D-Arg-Phe-Orn-NH$_2$, Hmt-D-Arg-Phe-Dab-NH$_2$, Hmt-D-Arg-Phe-Dap-NH$_2$, Mmt-D-Lys-Phe-Lys-NH$_2$, Mmt-D-Lys-Phe-Orn-NH$_2$, Mmt-D-Lys-Phe-Dab-NH$_2$, Mmt-D-Lys-Phe-Dap-NH$_2$, Mmt-D-Lys-Phe-Arg-NH$_2$, Tmt-D-Lys-Phe-Lys-NH$_2$, Tmt-D-Lys-Phe-Orn-NH$_2$, Tmt-D-Lys-Phe-Dab-NH$_2$, Tmt-D-Lys-Phe-Dap-NH$_2$, Tmt-D-Lys-Phe-Arg-NH$_2$, Hmt-D-Lys-Phe-Lys-NH$_2$, Hmt-D-Lys-Phe-Orn-NH$_2$, Hmt-D-Lys-Phe-Dab-NH$_2$, Hmt-D-Lys-Phe-Dap-NH$_2$, Hmt-D-Lys-Phe-Arg-NH$_2$, Mmt-D-Lys-Phe-Arg-NH$_2$, Mmt-D-Orn-Phe-Arg-NH$_2$, Mmt-D-Dab-Phe-Arg-NH$_2$, Mmt-D-Dap-Phe-Arg-NH$_2$, Mmt-D-Arg-Phe-Arg-NH$_2$, Tmt-D-Lys-Phe-Arg-NH$_2$, Tmt-D-Orn-Phe-Arg-NH$_2$, Tmt-D-Dab-Phe-Arg-NH$_2$, Tmt-D-Dap-Phe-Arg-NH$_2$, Tmt-D-Arg-Phe-Arg-NH$_2$, Hmt-D-Lys-Phe-Arg-NH$_2$ Hmt-D-Orn-Phe-Arg-NH$_2$, Hmt-D-Dab-Phe-Arg-NH$_2$, Hmt-D-Dap-Phe-Arg-NH$_2$, Hmt-D-Arg-Phe-Arg-NH$_2$, D-Arg-2'6'Dmt-Lys-Phe-NH$_2$, D-Arg-2'6'Dmt-Phe-Lys-NH$_2$, -continued D-Arg-Phe-Lys-2'6'Dmt-NH₂, D-Arg-Phe-2'6'Dmt-Lys-NH₂, D-Arg-Lys-2'6'Dmt-Phe-NH₂, D-Arg-Lys-Phe-2'6'Dmt-NH₂, Phe-Lys-2'6'Dmt-D-Arg-NH₂, Phe-Lys-D-Arg-2'6'Dmt-NH₂, Phe-D-Arg-2'6'Dmt-Lys-NH₂, Phe-D-Arg-Lys-2'6'Dmt-NH₂, Phe-2'6'Dmt-D-Arg-Lys-NH₂, Phe-2'6'Dmt-Lys-D-Arg-NH₂, Lys-Phe-D-Arg-2'6'Dmt-NH₂, Lys-Phe-2'6'Dmt-D-Arg-NH₂, Lys-2'6'Dmt-D-Arg-Phe-NH₂, Lys-2'6'Dmt-Phe-D-Arg-NH₂, Lys-D-Arg-Phe-2'6'Dmt-NH₂, Lys-D-Arg-2'6'Dmt-Phe-NH₂, D-Arg-2'6'Dmt-D-Arg-Phe-NH₂, D-Arg-2'6'Dmt-D-Arg-2'6'Dmt-NH₂, D-Arg-2'6'Dmt-D-Arg-Tyr-NH₂, D-Arg-2'6'Dmt-D-Arg-Trp-NH₂, Trp-D-Arg-Phe-Lys-NH₂, Trp-D-Arg-Tyr-Lys-NH₂, Trp-D-Arg-Trp-Lys-NH₂, Trp-D-Arg-2'6'Dmt-Lys-NH₂

D-Arg-Trp-Lys-Phe-NH₂,

D-Arg-Trp-Phe-Lys-NH₂,

D-Arg-Trp-Lys-2'6'Dmt-NH₂

D-Arg-Trp-2'6'Dmt-Lys-NH₂,

D-Arg-Lys-Trp-Phe-NH₂,

D-Arg-Lys-Trp-2'6'Dmt-NH₂,

Cha-D-Arg-Phe-Lys-NH₂,
or

Ala-D-Arg-Phe-Lys-NH₂.

16. The method of claim 15, wherein the mammal is a human.

17. The method of claim 15, wherein the peptide is administered orally, topically, intranasally, systemically, intravenously, subcutaneously, intramuscularly, intrathecally, or transdermally.

18. The method of claim 15, wherein the peptide is combined with a pharmaceutically acceptable carrier prior to administration to the mammal.

19. The method of claim 15, wherein the peptide has the amino acid sequence D-Arg-2'6'Dmt-Lys-Phe-NH₂.

20. The method of claim 15, wherein the peptide has the amino acid sequence 2'6'Dmt-D-Arg-Phe-Lys-NH₂.

21. The method of claim 15, wherein the peptide has the amino acid sequence Phe-D-Arg-Phe-Lys-NH₂.

* * * * *